United States Patent [19]

Berneth

[11] Patent Number: 4,835,270

[45] Date of Patent: * May 30, 1989

[54] CHROMOGENIC 3,1-BENZOXAZINES

[75] Inventor: Horst Berneth, Leverkusen, Fed. Rep. of Germany

[73] Assignee: Bayer Aktiengesellschaft, Leverkusen, Fed. Rep. of Germany

[ * ] Notice: The portion of the term of this patent subsequent to May 16, 2006 has been disclaimed.

[21] Appl. No.: 810,797

[22] Filed: Dec. 18, 1988

[30] Foreign Application Priority Data

Jan. 8, 1985 [DE] Fed. Rep. of Germany ....... 3500361

[51] Int. Cl.$^4$ .......................................... C07D 265/16
[52] U.S. Cl. ....................... 544/73; 544/74; 544/90; 544/95
[58] Field of Search ........................ 544/73, 74, 90, 95

[56]  References Cited
U.S. PATENT DOCUMENTS 3,839,447  10/1974  Swiger et al. ................... 260/562 P
4,070,508   1/1978  Ishige et al. ......................... 427/282

FOREIGN PATENT DOCUMENTS 2518096  11/1975  Fed. Rep. of Germany .
2530464   8/1976  Fed. Rep. of Germany .

OTHER PUBLICATIONS

Zaher et al., Chemical Abstracts, vol. 82(1975) 140038m.
Yoshida et al., Chemical Abstracts, vol. 92(1980) 2243135.
Schmidt et al., Chemical Abstracts, vol. 99(1983) 105086e.
Chemical Abstracts, vol. 70, No. 11, Mar. 17, 1969.
Chemical Abstracts, vol. 68, No. 5, Jan. 29, 1968.

Primary Examiner—Richard L. Raymond

Attorney, Agent, or Firm—Sprung Horn Kramer & Woods

[57] ABSTRACT

Compounds of the formula

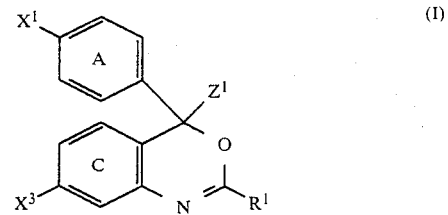

wherein
$Z^1$ denotes hydrogen, alkyl, cycloalkyl or

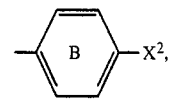

$R^1$ denotes hydrogen, alkyl, cycloalkyl, aralkyl, aryl, heteroalkyl or heteryl,
$X^1$, $X^2$ and $X^3$ denote hydrogen, halogen, alkyl, cycloalkyl, aryl, alkanoylamino, aroylamino or heteryl, and at least one of these radicals denotes $NH^1Y^2$, $OY^3$ or $SY^3$,
$Y^1$, $Y^2$ and $Y^3$ denote hydrogen, alkyl, cycloalkyl, aralkyl, aryl or heteryl and
$Y^1 + Y^2$ denote the remaining members of a 5-membered or 6-membered ring which optionally contains further hetero-atoms, are outstandingly suitable as colour-forming agents for pressure-sensitive, heat-sensitive and electrosensitive recording materials with an acid developer. Deep copies which are fast to light are obtained.

6 Claims, No Drawings

CHROMOGENIC 3,1-BENZOXAZINES

The invention relates to the use of chromogenic 3,1-benzoxazines of the formula

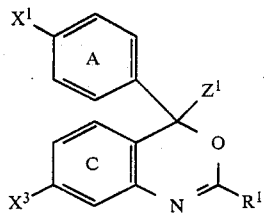

(I)

wherein
$Z^1$ denotes hydrogen, alkyl, cycloalkyl or

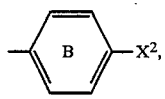

$R^1$ denotes hydrogen, alkyl, cycloalkyl, aralkyl, aryl, heteroalkyl or heteryl,
$X^1$, $X^2$ and $X^3$ independently of one another denote hydrogen, halogen, alkyl, cycloalkyl, aryl, alkanoylamino, aroylamino, heteryl, $NY^1Y^2$, $OY^3$ or $SY^3$, at least one of the radicals $X^1$, $X^2$ or $X^3$ representing $NY^1Y^2$, $OY^3$ or $SY^3$,
$Y^1$, $Y^2$ and $Y^3$ independently of one another denote hydrogen, alkyl, cycloalkyl, aralkyl, aryl or heteryl or the remaining members of a 5-membered or 6-membered ring which extends to one of the benzene-C atoms in the o-position and optionally contains further hetero-atoms, or
$Y^1 + Y^2$ denote the remaining members of a 5-membered or 6-membered ring which optionally contains further hetero-atoms and
the rings A, B and C and the radicals mentioned can in turn carry non-ionic radicals which are customary in dyestuff chemistry, or
the rings A, B and C can be benzo-fused,
for recording materials which are capable of pressure-copying or are thermoreactive or electrochromic and contain an acid colour developer.

Examples of non-ionic substituents which are customary in dyestuff chemistry are: halogen, hydroxyl, alkoxy, aryloxy, aralkoxy, heteryloxy, aryl, heteryl, alkylmercapto, arylmercapto, aralkylmercapto, alkylsulphonyl, cyano, carbamyl, alkoxycarbonyl, amino, which can be substituted by 1 or 2 alkyl, aryl or aralkyl groups or in which the substituents can be cyclised, alkenyloxy, alkylcarbonyloxy and arylcarbonyloxy, and, as substituents of the rings, also alkyl, aralkyl, nitro, alkenyl and arylvinyl.

Preferably, alkyl represents $C_1$–$C_{30}$-alkyl, in particular $C_1$–$C_{12}$-alkyl and especially $C_1$–$C_4$-alkyl, and alkenyl represents $C_2$–$C_5$-alkenyl.

Halogen is to be understood, in particular, as chlorine and bromine.

The alkyl radicals and the alkyl radicals in alkoxy, alkylthio, dialkylamino, alkanoylamino, alkylsulphonyl and alkoxycarbonyl groups can be branched and substituted, for example by fluorine, chlorine, $C_1$- to $C_4$-alkoxy, cyano or $C_1$–$C_4$-alkoxycarbonyl; particular examples are methyl, ethyl, propyl, 2-propyl, 2,2-dimethylpropyl, 2-butyl, 1-hexyl, 1-octyl, 1-dodecyl, 1-tetradecyl, 1-hexadecyl, 1-octadecyl, 2-bornyl-methyl, 2-chloro-ethyl, 2-cyanoethyl, 2-methoxy-ethyl, 2-ethoxycarbonylethyl and trifluoromethyl.

In particular, cycloalkyl is understood as meaning cyclohexyl, aryl is understood as meaning phenyl and naphthyl, aralkyl is understood as meaning benzyl and phenethyl, heteryl is understood as meaning pyridyl, pyrimidyl, pyrazinyl, triazinyl, imidazolyl, oxazolyl, thiazolyl, triazolyl, thiadiazolyl or tetrazolyl, which can be benzofused, and their partially hydrogenated or completely hydrogenated derivatives, and heteroalkyl is understood as meaning the rings or ring systems mentioned, which can be linked on via methylene or ethylene. The rings can be substituted by non-ionic substituents, in particular by $C_1$–$C_4$-alkyl, $C_1$–$C_4$-alkoxy, cyano, nitro or halogen.

The phenyl and naphthyl radicals and the radicals in benzyl or benzoylamino groups can carry up to 3 identical or different radicals.

Particular examples of substituted phenyl radicals are 2-, 3- or 4-tolyl, 2-, 3- or 4-anisyl, 2-, 3- or 4-chloro-phenyl, 2-, 3- or 4-nitro-phenyl, 2-, 3- or 4-cyanophenyl, 2-, 3- or 4-ethoxycarbonyl-phenyl, 2-, 3- or 4-methoxysulphonyl-phenyl, 2-, 3- or 4-trifluoromethylphenyl, 2,3-dinitrophenyl, 3,4-dimethyl-phenyl, 2-chloro-4-nitrophenyl, 3-chloro-4-nitro-phenyl, 5-chloro-2-methyl-4-nitro-phenyl, 4-chloro-3-methyl-phenyl, 3-chloro-4-methoxy-phenyl, 3-chloro-4-trifluoromethyl-phenyl, 3,4-dicyano-phenyl, 2,5-dichloro-4-cyano-phenyl and 2-methyl-1-naphthyl.

The heterocyclic radicals can carry up to 4 identical or different radicals. Particular examples are substituted heterocyclic radicals are 2-methyl-4-pyridyl, 4-nitro-2-pyridyl, 4-phenyl-thiazol-2-yl, 5-methyl-benzoxazolyl, 5-tert.-butyl-benzothiazolyl, 1,2-dimethyl-indol-3-or -5-yl and 2,2,6,6-tetramethyl-piperidin-4-yl.

Preferred alkanoyl are acetyl and propionyl, and preferred aryol is benzoyl.

The 3,1-benzoxazines of the formula (I) are usually colourless or at most slightly coloured.

Acid developers which may be mentioned in particular are clays, acid oxides and acid salts, as well as monomeric or polymeric phenols or carboxylic acids.

When the colour-forming agents are brought into contact with the acid developer, intense blue, green-blue, green, black, violet or red colour shades which are excellently fast to sublimation and light result. Navy blue, grey or black colorations can be achieved by mixtures with one another.

They are also useful as a mixture with one or more other known colour-forming agents, for example 3,3-bis(aminophenyl)-phthalides, 3,3-bis-(indolyl)-phthalides, 3-amino-fluoranes, spirodipyrans, chromenoindoles, phenoxazines, phenothiazines, carbazolylmethanes or other triarylmethane leuco-dyestuffs, in order to produce green, violet, blue, navy blue, grey or black colorations.

The 3,1-benzoxazines of the formula (I) exhibit a good colour intensity both on phenolic substrates and also, in particular, on activated clays. They are suitable, above all, as colour-forming agents for use in a heat-sensitive or pressure-sensitive recording material, which can be either a copying material or a registering material. Their rate of development is almost independent of the substituents. In general, they are distinguished by a high rate of development, with a simultaneously reduced sensitivity of the recording material to unintentional premature development. They can thereby be combined with one another almost as desired. The development colour shade is reached immediately without undesirable changes in shade occurring during or after the development.

The 3,1-benzoxazines of the formula (I) are distinguished by a good fastness to light and stability to ageing in the climate both in the developed and in the nondeveloped state.

A pressure-sensitive material consists, for example, of at least 1 pair of sheets which contain at least one colour-forming agent of the formula (I), dissolved or dispersed in a non-volatile organic solvent, and one acid developer.

Typical examples of such developers are active clay substances, such as attapulgus clay, acid clay, bentonite, montmorillonite, activated clay, for example acid-activated bentonite or montmorillonite, zeolite, halloysite, silicon dioxide, aluminum oxide, aluminium sulphate, aluminium phsophate, zinc chloride or activated kaolin. Other developers are organic compounds with an acid reaction, such as optionally ring-substituted phenols, salicylic acid or salicylic acid esters and metal salts thereof, and furthermore, in particular, polymeric material with an acid reaction, for example a phenolic polymer, an alkylphenol/acetylene resin, a maleic acid/colophonium resin or a partly or completely hydrolysed polymer or maleic anhydride with styrene, ethylene or vinyl methyl ether or carboxypolymethylene. Mixtures of the polymeric compounds mentioned can also be employed. Preferred developers are acid clay, acid-activated bentonite or montmorillonite, zinc salicylates or the condensation products of p-substituted phenols with formaldehyde. The latter can also contain zinc.

The developers can additionally also be employed as a mixture with other pigments which are non-reactive per se or of low reactivity.

At the points where the colour-forming agent comes into contact with the developer, it produces a coloured marking. In order to prevent premature activation of the colour-forming agents present in the pressure-sensitive recording material, these agents are as a rule separated from the developer. This can advantageously be achieved by incorporating the colour-forming agents into foam-like, sponge-like or honeycombed structures. The colour-forming agents are preferably enclosed in microcapsules, which as a rule can be crushed by pressure. Processes for the preparation of such microcapsules are known.

Examples of suitable non-volatile solvents are partially hydrogenated terphenyl, alkylated naphthalenes or dibutyl phthalate.

An arrangement in which the encapsulated colour-forming agent is present on the reverse side of a transfer sheet in the form of a layer and the electron acceptor is present on the front side of a receiver sheet in the form of a layer is preferred.

Another arrangement of the constituents consists of the microcapsules, containing the colour-forming agent, and the developer in or on the same sheet in the form of one or more individual layers or in the paper pulp.

The compounds of the formula (I) can preferably also be used as colour-forming agents in a thermoreactive recording material. This as a rule contains at least one layer carrier, one colour-forming agent, one developer and, if appropriate, also a binder.

Thermoreactive recording systems include, for example, heat-sensitive recording and copying materials and papers. These systems are used, for example, for recording information, for example in electronic computers, remote printers or telex machines or in recording equipment and measurement instruments, such as, for example, electrocardiographs. Image production (marking) can also be effected manually with a heated pen. Laser beams are another device for producing markings by means of heat.

The thermoreactive recording material can be built up such that the colour-forming agent is dissolved or dispersed in a binder layer and the developer is dissolved or dispersed in the binder in a second layer. Another possibility consists in dispersing both the colour-forming agent and the developer in one layer. The binder is softened in specific regions by means of heat, and at these points where heat is applied, the colour-forming agent comes into contact with the developer and the desired colour develops immediately.

Suitable developers are the same substances such as are used in pressure-sensitive papers. In this case, substances which are preferably used are phenolic resins or phenolic compounds, such as are described, for example, in German Patent Specification No. 1,251,348, for example 4-tert.-butyl-phenol, 4-phenyl-phenol, 4-hydroxy-diphenyl ether, α-naphthol, β-naphthol, methyl 4-hydroxy-benzoate, 4-hydroxy-acetophenone, 2,2'-dihydroxydiphenyl, 4,4'-iso-propylidene-diphenol, 4,4'-isopropylidene-bis-(2-methylphenol), 4,4'-bis-(hydroxyphenyl)-valeric acid, hydroquinone, pyrogallol, fluoroglucine, p-, m- or o-hydroxy-benzoic acid, gallic acid or 1-hydroxy-2-naphthoic acid, as well as boric acid and dicarboxylic acids, preferably aliphatic dicarboxylic acids, for example tartaric acid, oxalic acid, maleic acid, citric acid, citraconic acid or succinic acid.

Fusible, film-forming binders are preferably used for the preparation of the thermoreactive recording material. These binders are usually water-soluble, whilst the 3,1-benzoxazines and the developer are sparingly soluble or insoluble in water.

The binders should be capable of dispersing and fixing the colour-forming agent and the developer at room temperature.

Under the action of heat, the binder softens or melts, so that the colour-forming agent comes into contact with the developer and a colour can form. Binders which are water-soluble or at least water-swellable are, for example, hydrophilic polymers, such as polyvinyl alcohol, polyacrylic acid, hydroxyethylcellulose, methylcellulose, carboxymethylcellulose, polyacrylamide, polyvinylpyrrolidone, gelatine and starch.

The thermoreactive layers can contain further additives: to improve the degree of whiteness, to facilitate printing of the paper, to prevent the heated pen from sticking and for colour formation only within a limited temperature range.

Another suitable thermoreactive recording system is described in German Offenlegungsschrift No. 3,337,296. Acid-modified polymers, preferably of acrylonitrile, are used there as developers.

The process and formulations described are known, for example, from U.S. Patent Specifications Nos. 2,948,753, 3,096,189 and 3,193,404 and from German Offenlegungsschriften Nos. 2,555,080 and 2,700.937.

The invention furthermore relates to chromogenic 3,1-benzoxazines of the formula (I) wherein $Z^1$, $R^1$, $X^1$, $X^2$, $X^3$, A, B and C have the meaning given in the case of formula (I), and wherein, if the rings A and B do not carry further substituents or fused-on systems and
if $X^3$ represents hydrogen, dialkylamino or diaralkylamino
$X^1$ and $X^2$ are not simultaneously dimethylamino, or
if $R^1$ represents

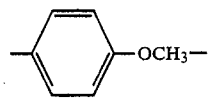

$X^1$ and $X^2$ are not simultaneously methoxy, or
if $Z^1$ represents hydrogen
$X^1$ is not $C_1$- to $C_3$-alkoxy.

Preferred chromogenic 3,1-benzoxazines are those of the formula

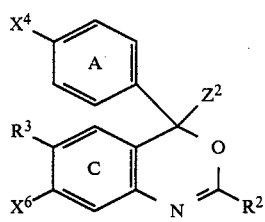

wherein
one of the radicals $X^6$ or $R^3$ denotes $NY^4Y^5$, $OY^6$ or $SY^6$ and the other denotes hydrogen, $C_1$-$C_{18}$-alkyl, which can be substituted by fluorine, chlorine, bromine, $C_1$-$C_8$-alkoxy, cyano and/or $C_1$-$C_{18}$-alkoxycarbonyl, cyclohexyl, or benzyl, phenyl, biphenylyl or naphthyl radicals which can be substituted by chlorine, $C_1$-$C_8$-alkyl, $C_1$-$C_8$-alkoxy, cyano, $C_1$-$C_4$-alkoxycarbonyl and/or $C_1$-$C_4$-alkanoylamino, or $C_1$-$C_8$-alkanoylamino or benzoylamino, which can be substituted by chlorine, $C_1$-$C_4$-alkyl and/or $C_1$-$C_4$-alkoxy, $X^2$ denotes hydrogen, $C_1$-$C_8$-alkyl, cyclohexyl or

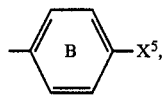

$R^2$ denotes hydrogen, $C_1$-$C_{18}$-alkyl which optionally carries fluorine, chlorine, bromine, $C_1$-$C_8$-alkoxy, cyano or $C_1$-$C_{18}$-alkoxycarbonyl, cyclohexyl, or benzyl, phenyl, biphenylyl, terphenylyl, naphthyl, picolyl, pyridyl, quinolyl, pyrimidyl, pyrazinyl, triazinyl, triazolyl, triazolylmethyl, thiadiazolyl, tetrazolyl, indolyl or optionally benzofused imidazole, oxazole or thiazole radicals which optionally carry fluorine, chlorine, bromine, nitro, $C_1$-$C_{18}$-alkyl, $C_1$-$C_{18}$-alkoxy, $C_1$-$C_{18}$-alkylthio, $C_1$-$C_{18}$-mono- or dialkylamino, $C_1$-$C_{18}$-alkylsulphonyl, cyano, $C_1$-$C_{18}$-alkoxycarbonyl and/or $C_1$-$C_{18}$-alkanoylamino,
$X^4$ and $X^5$ independently of one another denote hydrogen, fluorine, chlorine, bromine or $C_1$-$C_{18}$-alkyl, $C_1$-$C_{18}$-alkyl which is optionally substituted by fluorine, chlorine, nitro, hydroxyl, $C_1$-$C_8$-alkoxy, $C_1$-$C_8$-alkylthio, cyano, $C_1$-$C_8$-alkoxycarbonyl, $C_1$-$C_8$-alkanoyloxy, amino and/or mono- or di-$C_1$-$C_4$-alkylamino, phenyl which is optionally substituted by chlorine and/or $C_1$-$C_{12}$-alkyl, $C_1$-$C_{12}$-alkanoylamino, benzoylamino which is optionally substituted by chlorine and/or $C_1$-$C_{12}$-alkyl, indolyl or piperidyl radicals which are optionally substituted by $C_1$-$C_4$-alkyl, $C_1$-$C_4$-alkoxy, chlorine and/or phenyl, $NY^4Y^5$, $OY^6$ or $SY^6$,
but wherein
at most two of the radicals $X^4$, $X^5$ and $X^6$ are $NY^4Y^5$,
$Y^4$, $Y^5$ and $Y^6$ independently of one another denote hydrogen, $C_1$-$C_{18}$-alkyl which is optionally substituted by chlorine, hydroxyl, di-$C_1$-$C_4$-alkylamino, cyano, $C_1$-$C_4$-alkoxycarbonyl, $C_1$-$C_4$-alkanoyloxy or $C_1$-$C_4$-alkoxy, cyclohexyl or phenyl or benzyl, which can be substituted by chlorine, $C_1$-$C_{12}$-alkyl or $C_1$-$C_{12}$-alkoxy, piperidyl which is optionally substituted by $C_1$-$C_4$-alkyl, or members which, together with the N or O to which they are bonded and one of the rings A, B or C, are necessary to complete a ring system of the following formula

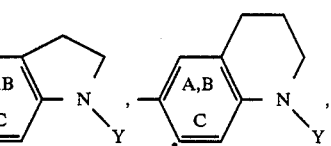

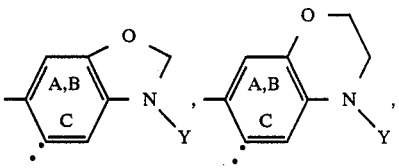

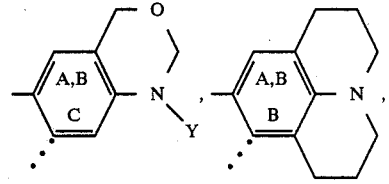

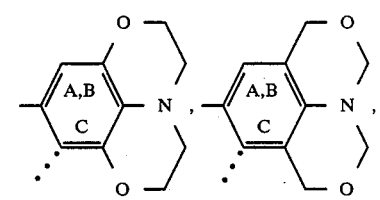

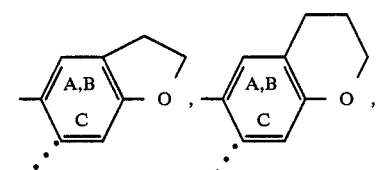

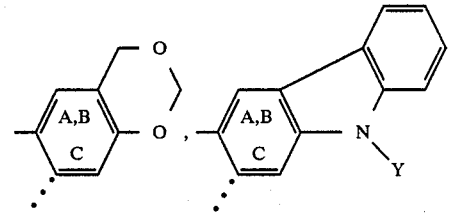

wherein the broken line denotes further fusing-on in the case of ring C,

Y represents hydrogen, $C_1$- to $C_{18}$-alkyl, which can be substituted by chlorine, cyano, $C_1$- to $C_4$-alkoxycarbonyl or $C_1$- to $C_4$-alkoxyl, cyclohexyl, or phenyl or benzyl, which can be substituted by chlorine, $C_1$- to $C_{12}$-alkyl or $C_1$- to $C_{12}$-alkoxy, the saturated ring part can carry up to 4 radicals from the group comprising chlorine, $C_1$- to $C_4$-alkyl, $C_1$- to $C_4$-alkoxy and phenyl, the rings A, B and C can be substituted by chlorine, $C_1$–$C_4$-alkyl, $C_1$–$C_4$-alkoxy, phenoxy or phenylamino which is optionally substituted by chlorine, $C_1$–$C_4$-alkyl or $C_1$–$C_4$-alkoxy and/or $C_1$–$C_4$-alkanoylamino or benzo-fused, or $NY^4Y^5$ denotes a pyrrolo, pyrrolidino, piperidino, pipecolino, pyrazino, morpholino, pyrazolo or pyrazolino radical which is optionally substituted by chlorine, $C_1$–$C_4$-alkyl or aryl, in particular phenyl.

Particularly preferred chromogenic 3,1-benzoxazines are those of the formula $$\text{(III)}$$

wherein $X^8$ denotes hydrogen, chlorine, bromine, $C_1$–$C_{18}$-alkyl which is optionally substituted by chlorine and/or $C_1$–$C_4$-alkoxy, phenyl which is optionally substituted by chlorine and/or $C_1$–$C_4$-alkeyl, $C_1$–$C_4$-alkanoylamino, benzoylamino which is optionally substituted by chlorine and/or $C_1$–$C_4$-alkyl, indolyl or piperidyl radicals which are optionally substituted by methyl, ethyl, methoxy, chlorine and/or phenyl, $OY^9$ or $SY^9$, $X^7$ denotes $NY^7Y^{7\prime}$ or independently has the meaning of $X^8$, $R^4$ denotes hydrogen, $C_1$–$C_{18}$-alkyl which optionally carries fluorine, chlorine or $C_1$–$C_4$-alkoxy, cyclohexyl, benzyl which optionally carries chlorine and/or $C_1$–$C_{18}$-alkyl, or phenyl, biphenylyl, naphthyl, picolyl, pyridyl, quinolyl, pyrimidyl, pyrazinyl, triazolyl, thiadiazolyl, indolyl or optionally benzo-fused imidazole, oxazole or thiazole radicals which optionally carry chlorine, bromine, nitro, $C_1$–$C_8$-alkyl, $C_1$–$C_8$-alkoxy, $C_1$–$C_8$-alkylthio, $C_1$–$C_8$-dialkylamino, $C_1$–$C_8$-alkylsulphonyl, cyano, $C_1$–$C_8$-alkoxycarbonyl and/or $C_1$–$C_8$-alkanoylamino, $R^5$, $R^6$, $R^7$ and $R^8$ independently of one another denote hydrogen, chlorine, bromine, $C_1$–$C_4$-alkyl, $C_1$–$C_4$-alkoxy, $C_1$–$C_4$-alkylthio, amino, $C_1$–$C_4$-mono-or dialkylamino, $C_1$–$C_4$-alkanoylamino, or $C_1$–$C_4$-alkylsulphonylamino, or benzoylamino, anilino or N-$C_1$–$C_4$-alkylanilino radicals which are optionally substituted by methyl, methoxy, ethoxy or chlorine, $Y^7$ to $Y^9$ independently of one another denote $C_1$–$C_8$-alkyl which is optionally substituted by chlorine, cyano, methoxycarbonyl, methoxycarbonyloxy, acetyloxy, hydroxyl, methoxy, ethoxy or dimethylamino, cyclohexyl, benzyl, phenyl, which can be substituted by chlorine, cyano, methyl, ethyl, methoxy or ethoxy, or 2,2,6,6-tetramethyl-or 1,2,2,6,6-pentamethyl-piperidin-4-yl, $Y^{7\prime}$ and $Y^{8\prime}$ denote hydrogen or have the meaning of $Y^7$ or $Y^8$ respectively, or $NY^7Y^{7\prime}$ and $NY^8Y^{8\prime}$ independently of one another represent a pyrrolidino, piperidino, piperazino, morpholino or pyrazolino radical which is substituted by $C_1$–$C_4$-alkyl and/or phenyl, which can also carry chlorine, methyl, methoxy, ethoxy or cyano.

In especially preferred compounds of the formula (III), $X^8$ represents $X^{8\prime}$=hydrogen, chlorine, $C_1$–$C_4$-alkyl, $C_1$–$C_4$-alkoxy, benzyloxy, phenoxy, methylthio, ethylthio, phenyl, tolyl, chlorophenyl, acetylamino, propionylamino, benzoylamino or chlorobenzoylamino, $X^7$ represents $X^{7\prime}=NY^{7\prime\prime}Y^{7\prime\prime\prime}$ or independently has the meaning of $X^{8\prime}$, $R^4$ represents $R^{4\prime}$=hydrogen, methyl, trifluoromethyl, ethyl, propyl, butyl, tert.-butyl, pentyl, hexyl, heptyl, hept-3-yl, octyl, cyclohexyl, benzyl, phenyl, chlorophenyl, tolyl, tert.-butylphenyl, anisyl, nitrophenyl, cyanophenyl, methoxycarbonylphenyl, methylsulphonylphenyl, chloronitrophenyl, dichlorophenyl, biphenylyl, naphthyl, pyridyl, picolyl, quinolyl, 2-, 3- or 5-indolyl or 5-benzoxazolyl, $R^5$ represents $R^{5\prime}$ and $R^8$ represents $R^{8\prime}$=hydrogen, chlorine, methyl, ethyl, methoxy, ethoxy, amino, methylamino, acetylamino, benzoylamino or methylsulphonylamino, $R^6$ represents $R^{6\prime}$=hydrogen, chlorine, bromine, methyl, ethyl, methoxy, ethoxy, acetylamino or methylsulphonylamino, $R^7$ represents $R^{7\prime}$=hydrogen, chlorine, bromine, methyl, ethyl, propyl, butyl, methoxy, ethoxy, acetylamino, benzoylamino or methylsulphonylamino, $Y^8$ represents $Y^{8\prime\prime}$ and $Y^{8\prime}$ represents $Y^{8\prime\prime\prime}$, wherein $Y^{7\prime\prime}$ and $Y^{8\prime\prime}$ denote methyl, ethyl, propyl, butyl, cyanoethyl, methoxyethyl, ethoxyethyl, methoxycarbonylethyl, methoxycarbonyloxyethyl, acetyloxyethyl, benzyl, phenyl, 4-tolyl, 4-chlorophenyl, 4-anisyl, 4-ethoxyphenyl or 4-cyanophenyl, $Y^{7\prime\prime\prime}$ and $Y^{8\prime\prime\prime}$ denote hydrogen or have the meaning of $Y^{7\prime\prime}$ and $Y^{8\prime\prime}$ respectively, or $NY^{7\prime\prime}Y^{7\prime\prime\prime}$ and $NY^{8\prime\prime}Y^{8\prime\prime\prime}$ denote

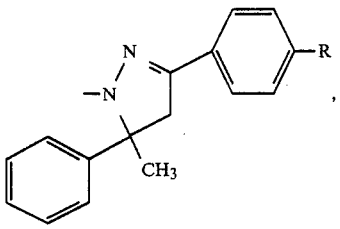

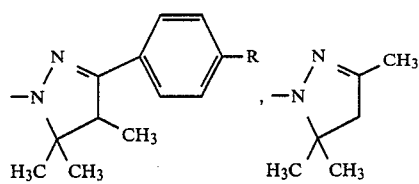

and

R denotes hydrogen, chlorine, methyl, methoxy, ethoxy or cyano.

Chromogenic 3,1-benzoxazines which are likewise particularly preferred are those of the formula

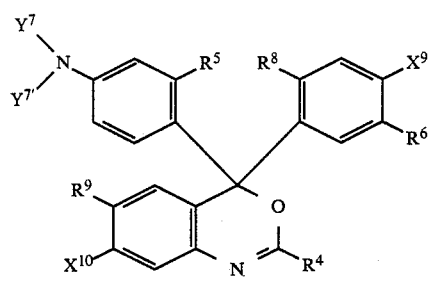

(IV)

wherein $X^9$ denotes hydrogen, chlorine, bromine, $C_1$-$C_{18}$-alkyl which is optionally substituted by chlorine and/or $C_1$-$C_4$-alkoxy, phenyl which is optionally substituted by chlorine and/or $C_1$-$C_4$-alkyl, $C_1$-$C_4$-alkanoylamino, benzoylamino which is optionally substituted by chlorine and/or $C_1$-$C_4$-alkyl, indolyl or piperidyl radicals which are optionally substituted by methyl, ethyl, methoxy, chlorine and/or phenyl, $NY^{10}Y^{10'}$, $OY^9$ or $SY^9$, $X^{10}$ denotes $OY^{11}$ or $SY^{11}$ and $R^9$ denotes hydrogen, chlorine, bromine, $C_1$-$C_4$-alkyl, $C_1$-$C_4$-alkoxy, $C_1$-$C_4$-alkylthio, $C_1$-$C_4$-alkanoylamino, benzoylamino or $C_1$-$C_4$-alkylsulphonylamino, or $X^{10}$ denotes hydrogen, chlorine, bromine, $C_1$-$C_{18}$-alkyl which is optionally substituted by chlorine and/or $C_1$-$C_4$-alkoxy, phenyl which is optionally substituted by chlorine and/or $C_1$-$C_4$-alkyl, $C_1$-$C_4$-alkanoylamino, benzoylamino which is optionally substituted by chlorine and/or $C_1$-$C_4$-alkyl, or indolyl or piperidyl radicals which are optionally substituted by methyl, ethyl, methoxy, chlorine and/or phenyl and $R^9$ denotes $C_1$-$C_4$-alkoxy, $C_1$-$C_4$-alkylthio, amino or $C_1$-$C_4$-mono- or dialkylamino, or anilino or N-$C_1$-$C_4$-alkylanilino which is optionally substituted by methyl, methoxy, ethoxy or chlorine, $R^4$, $R^5$, $R^6$ and $R^8$ have the meaning given under formula (III) and $Y^7$, $Y^{7'}$, $Y^9$ to $Y^{11}$, $Y^{10'}$, $NY^7Y^{7'}$ and $NY^{10}Y^{10'}$ have the meaning given for $Y^7$, $Y^{7'}$ and $NY^7Y^{7'}$ respectively under formula (III).

In especially preferred compounds of the formula (IV), $X^9$ represents $X^{9'}$=hydrogen, chlorine, $C_1$-$C_4$-alkyl, $C_1$-$C_4$-alkoxy, benzyloxy, phenoxy, methylthio, ethylthio, phenyl, tolyl, chlorophenyl, acetylamino, propionylamino, benzoylamino, chlorobenzoylamino or $NY^{10''}Y^{10'''}$, $X^{10}$ represents $X^{10'}$=$C_1$-$C_6$-alkoxy, benzyloxy, phenoxy, methylthio or ethylthio and $R^9$ represents $R^{9'}$=hydrogen, chlorine, methyl, ethyl, propyl, butyl, methoxy, ethoxy, acetylamino, benzoylamino or methylsulphonylamino, or $X^{10}$ represents $X^{10''}$=hydrogen, chlorine, $C_1$-$C_4$-alkyl, phenyl, acetylamino, propionylamino, benzoylamino or chlorobenzoylamino and $R^9$ represents $R^{9''}$=methoxy, ethoxy, methylthio, amino, ethylamino, dimethylamino, anilino, N-methyl-4-methyl-anilino or N-methyl-4-ethoxy-anilino, $R^4$, $R^5$, $R^6$ and $R^8$ represent $R^{4'}$, $R^{5'}$, $R^{6'}$ and $R^{8'}$ respectively, with the meaning given under formula (III), $Y^7$ represents $Y^{7''}$ and $Y^{7'}$ represents $Y^{7'''}$, wherein $Y^{7''}$, $Y^{7'''}$, $Y^{10''}$ and $NY^{7''}Y^{7'''}$ and $NY^{10''}Y^{10'''}$ have the meaning given for $Y^{7''}$, $Y^{7'''}$ and $NY^{7''}Y^{y''''}$ under formula (III).

Chromogenic 3,1benzoxazines which are likewise particularly preferred are those of the formula

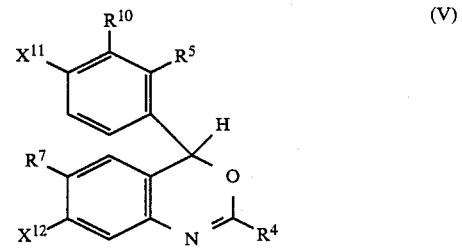

(V)

wherein $X^{11}$ and $X^{12}$ denote $NY^{12}Y^{12'}$, $OY^{13}$ or $SY^{13}$ and $R^4$, $R^5$ and $R^7$ have the meaning given in the case of formula (III), $R^{10}$ has the meaning given for $R^6$ in the case of formula (III) and $Y^{12}$, $Y^{12'}$, $Y^{13}$ and $NY^{12}Y^{12'}$ have the meaning given for $Y^7$, $Y^{7'}$ and $NY^7Y^{7'}$ respectively in the case of formula (III).

In especially preferred compounds of the formula (V), $X^{11}$ and $X^{12}$ represent $X^{11'}$ and $X^{12'}$=$C_1$-$C_4$-alkoxy, benzyloxy, phenoxy, methylthio, ethylthio or $NY^{12''}Y^{12'''}$, $R^4$, $R^5$ and $R^7$ represent $R^{4'}$, $R^{5'}$ and $R^{7'}$, with the meaning given under formula (III), $R^{10}$ represents $R^{10'}$, with the meaning given for $R^{6'}$ under formula (III), and $Y^{12''}$, $Y^{12'''}$ and $NY^{12''}Y^{12'''}$ have the meaning given for $Y^{7''}$, $Y^{7'''}$ and $NY^{7''}Y^{7'''}$ respectively under formula (III).

The abovementioned 3,1-benzoxazines of the formulae (II) to (V) are colour-forming agents which can preferably be used.

The invention furthermore relates to leuco compounds of the formula

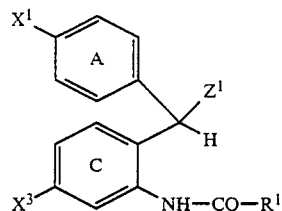 (VI)

wherein $R^1$, $Z^1$, $X^1$, $X^2$, $X^3$, A, B and C have the abovementioned meaning, and preferably the meaning given in the case of formulae (II) to (V).

The invention furthermore relates to a process for the preparation of a 3,1-benzoxazine of the formulae (I) to (V), characterised in that an amide of the formula

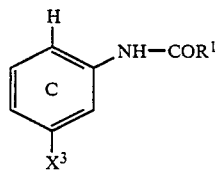 (VII)

is reacted with a ketone or aldehyde of the formula

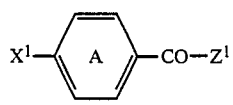 (VIII)

or an aromatic compound of the formula

 (IX)

is reacted with a ketone of the formula

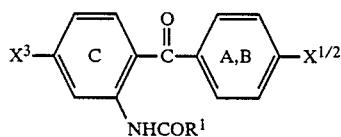 (X)

wherein $R^1$, $Z^1$, $X^1$, $X^2$, $X^3$, A, B and C have the abovementioned meaning.

The compounds (VII) and (IX) are, in particular, those in which $X^1$, $X^2$ or $X^3$ is an electron donor substituent, such as $NY^1Y^2$, $OY^3$ or $SY^3$, wherein $Y^1$ or $Y^3$ have the abovementioned meaning and the rings A, B and C are not deactivated by powerful electron acceptor substituents, such as, for example, nitro, cyano or alkoxycarbonyl.

The reaction is usually carried out with reagents which split off water, without or with solvents which are inert under these conditions at temperatures between 0° C. and the boiling point of the particular medium. The mixture is then poured onto, for example, water or an alcohol, if necessary after removal of the inert solvent. The 3,1-benzoxazines of the formula (I) are obtained by increasing the pH value with, for example, alkali metal or alkaline earth metal hydroxides, carbonates, bicarbonates, ammonia or amines until the colour disappears. It may be necessary, here, to split off water from any carbinol bases formed, to warm the mixture for some time or to treat the impure product primarily obtained for some time in solvents, such as alcohols—for example methanol, ethanol, 2-propanol or butanol; nitriles—for example acetonitrile; ketones—for example acetone or 2-butanone; (chloro)hydrocarbons—for example toluene, chlorobenzene, dichlorobenzene, chloroform or 1,2-dichloroethane; or esters—for example ethyl acetate or butyl acetate, at temperatures between room temperature and the boiling point of the particular medium.

Examples of reagents which split off water are phosphorus oxychloride, phosphorus pentachloride, diphosphorus pentoxide, triphenylphosphine dichloride, phosgene, phosphorus trichloride, phosphorus tribromide, sulphuryl chloride, thionyl chloride, oxalyl chloride or mixtures thereof. Phosphorus oxychloride and phosphorus oxychloride/diphosphorus pentoxide are preferably employed.

Examples of suitable inert solvents are toluene, chlorobenzene, dichlorobenzene, nitrobenzene and chlorinated aliphatic hydrocarbons, such as 1,2-dichloroethane.

The 3,1-benzoxazines of the formula (I) can also be prepared by oxidation of leuco compounds of the formula

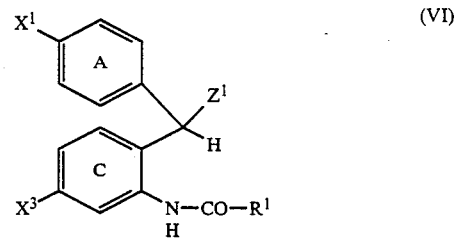 (VI)

wherein $R^1$, $Z^1$, $X^1$, $X^2$, $X^3$, A, B and C have the abovementioned meaning.

This oxidation can be carried out in a known manner with relatively highly valent metal compounds, such as $PbO_2$, $MnO_2$, permanganates, $CrO_3$, chromates, dichromates, $NiO_2$ or $K_3[Fe(CN)_6]$, with quinones, such as chloranil, tetrachloro-o-quinone or dichloro-dicyanoquinone, or in another manner known from the literature, such as, for example, with oxygen, air, perborates or hydrogen peroxide.

The compounds are worked up, isolated and if necessary after-treated in a manner analogous to that described above.

Oxidation with relatively highly valent metal compounds is usually carried out in an acid medium or in organic solvents, such as alcohols—for example ethanol, isopropanol or ethylene glycol monomethyl ether; ketones— for example acetone, butanone or methyl isopropyl ketone; or polar aprotic solvents, for example N-methyl-pyrrolidone, γ-butyrolactone, acetonitrile, dimethylsulphoxide or sulpholane, or in mixtures of such solvents with acids at temperatures between 0° C. and 60° C., preferably 10°–40° C.

Examples of suitable acids are hydrochloric acid, sulphuric acid, phosphoric acid, acetic acid, propionic acid or mixtures with one another and/or mixtures with water. A preferred mixture is hydrochloric acid, acetic acid and water.

Oxidation with quinones is usually carried out in organic solvents, such as alcohols—for example methanol, ethanol or isopropanol; ketones—for example acetone or butanone; esters, for example ethyl acetate or butyl acetate; carboxylic acids—for example acetic acid or propionic acid; or polar aprotic solvents, such as N-methylpyrrolidone, dimethylformamide, γ-butyrolactone, acetonitrile or sulpholane, or in mixtures thereof at temperatures between 0° C. and the boiling point of the medium, preferably 20°–70° C.

The leuco compounds of the formula (VI) can be incorporated into customary pressure-reactive or thermoreactive papers, for example, as colour-forming agents which develop slowly. Because of their good fastness to light, they serve there as mixing components for colour-forming agents which develop rapidly but are not very stable to light, for example crystal violet lactone. The fastness to light of the recording is thus improved.

The leuco compounds of the formula (VI) are also suitable for pressure-reactive or thermo-reactive recording materials which develop oxidatively. Here, a suitable oxidising agent is added to the colour-forming agent or to the developer, and further processing of the layers is similar to that for customary thermo-sensitive or pressure-sensitive recording materials. By contact with the oxidising agent, the leuco compound is oxidised to the dyestuff and thus gives a coloured marking.

The 3,1-benzoxazines of the formula (I) and the dyestuffs formed therefrom by ring-opening are suitable for dyeing polyacrylonitrile, tanned cotton and other acid-modified fibres, fabircs and powders.

EXAMPLE 1

270 g of Michler's hydrol and 137 g of 3-methoxy-4-methyl-aniline are refluxed in 1 l of methanol and 5 ml of concentrated hydrochloric acid for 2 hours. After cooling, the precipitate is filtered off with suction, washed with methanol and dried. Recrystallisation from toluene gives 230 g (59% of theory) of colourless crystals of melting point 190° to 192° C. and of the formula

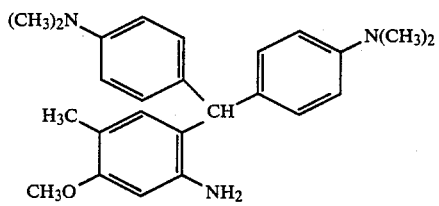

38.9 g of this compound are suspended in 100 ml of 1,2-dichloroethane. 17.5 g of 4-chloro-benzoyl chloride in 50 ml of 1,2-dichloro-ethane are added dropwise. After 1 hour at 30° to 40° C., the solvent is removed in vacuo, the residue is taken up in 150 ml of ethanol and the mixture is neutralised with 10% strength sodium hydroxide solution. The thick suspension is filtered with suction and the precipitate is washed with ethanol/water 3/1 and dried. 50.9 g (96% of theory) of colourless crystals of melting point 229° to 231° C. and of the formula

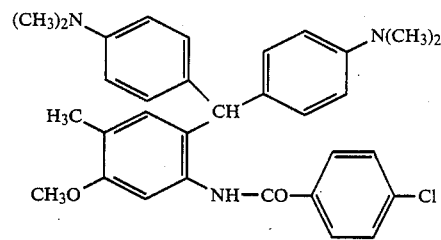

are obtained.

IR (KBr): 1673 and 1610 cm$^{-1}$.

26.4 g of this leuco compound are stirred in 30 ml of dimethylformamide with 12.3 g of chloranil at 65° C. for 1.5 hours. After cooling, the mixture is diluted with 100 ml of methanol and decolorised with 17 ml of triethylamine and the precipitate is filtered off with suction and washed with methanol. While still moist, the product is stirred in 50 ml of acetonitrile, filtered off with suction and dried:

22.8 g (87% of theory) of pale greenish crystals of melting point 237° to 239° C. and of the formula

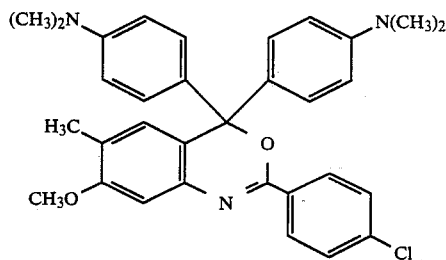

IR (KBr): 1610 cm$^{-1}$.

A solution in glacial acetic acid becomes bluish-tinged green with $\lambda_{max}=475$, 622 nm. A turquois intense coloration is obtained on acid clay, and a bluish-tinged green intense coloration is obtained with bisphenol A.

EXAMPLE 2

The compound of the formula

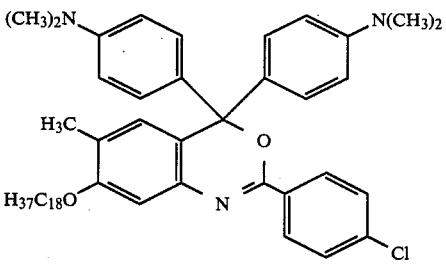

with a melting point of 111° to 113° C. is obtained analogously to Example 1.

IR (KBr): 1610 cm$^{-1}$.

A solution in glacial acetic acid becomes bluish-tinged green with $\lambda_{max}=475$, 622 nm. A turquoise intense coloration is achieved on acid clay, and a bluish-tinged green intense coloration is achieved on bisphenol A.

The compounds of Examples 3 to 9 can be prepared analogously.

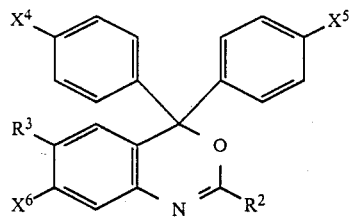

| Example | $X^4$ | $X^5$ | $X^6$ | $R^3$ | $R^2$ | Colour shade on acid clay or with bisphenol A |
|---|---|---|---|---|---|---|
| 3 | $(C_2H_5)_2N$ | $(C_2H_5)_2N$ | $CH_3O$ | $CH_3$ | cyclohexyl (with H) | turquoise |
| 4 | $H_2N$ | $H_2N$ | phenyl-$CH_2O$ | $C_4H_9$ | phenyl-$OCH_3$ | turquoise |
| 5 | $(CH_3)_2N$ | morpholino (O-N–) | $C_2H_5O$ | Cl | phenyl-$CH_3$ | bluish-tinged green |
| 6 | $(CH_3)_2N$ | 2,2,6,6-tetramethylpiperidinyl | $CH_3O$ | $CH_3$ | $-C_2H_5$ | bluish-tinged green |
| 7 | $(C_2H_5)_2N$ | $(NCC_2H_4)_2N$ | H | $CH_3O$ | pyridyl | bluish-tinged green |
| 8 | $(CH_3)_2N$ | $ClC_2H_4$, $CH_3$–N | phenyl-O | $CH_3$ | 2,3-dichlorophenyl | bluish-tinged green |
| 9 | $(CH_3)_2N$ | $(CH_3)_2N$ | phenyl-CO—NH | H | 2-methyl-1-methyl-5-methylindol-3-yl | bluish-tinged green |

EXAMPLE 10

A mixture of 28.3 g of 4-(diethylamino)-4'-methoxybenzophenone and 27.5 g of 3-(dimethylamino)-4'-chlorobenzanilide is introduced into a mixture of 76.5 g of phosphorus oxychloride and 42.5 g of phosphorus pentoxide, while cooling. The melt is stirred at 20° to 25° C. for 72 hours and at 35° to 40° C. for 24 hours. It is taken up in 100 ml of acetonitrile and the mixture is poured onto a mixture of 200 ml of chloroform and 500 g of ice at 0° C. It is now brought to pH 11 at 0° to 5° C. with concentrated sodium hydroxide solution and is kept at this pH during thawing. The chloroform phase is separated off and dried over sodium sulphate. The solvent is removed in vacuo, the residue is dissolved in 100 ml of toluene and the solution is stirred vigorously with 500 ml of 5% strength hydrochloric acid. The toluene phase is separated off and the aqueous phase is extracted three times more with 100 ml of toluene each time. Finally, the acid aqueous phase is added dropwise to a solution of 40 g of sodium hydroxide in 500 ml of water. The precipitate is filtered off with suction, washed with water and, while still moist, introduced into 300 ml of ethanol. The suspension is heated up to 60° C., cooled and filtered with suction. After drying, the product is stirred again with 100 ml of acetone and 2 ml of triethylamine, filtered off with suction and washed with acetone. After drying, 19.4 g (36% of theory) of a colourless crystalline powder of melting point 164° to 165° C. and of the formula are obtained.

IR (KBr): 1600 cm$^{-1}$.

A solution in glacial acetic acid becomes deep green with $\lambda_{max}=482, 629$ nm. An intense green coloration is achieved on acid clay and with bisphenol A.

EXAMPLE 11

The compound of the formula is obtained analogously in a 31% yield.

A solution in glacial acetic acid becomes deep green with $\lambda_{max}=482, 630$ nm. An intense green coloration is achieved on acid clay and with bisphenol A.

EXAMPLE 12

The compound of the formula with a melting point of 118° to 120° C. is obtained analogously in a 43% yield.

A solution in glacial acetic acid becomes deep green with $\lambda_{max}=444, 648$ nm. An intense yellowish-tinged green coloration is achieved on acid clay and with bisphenol A.

EXAMPLE 13

The compound of the formula with a melting point of 178°–179° C. is obtained analogously in a 59% yield.

IR: 1598 cm$^{-1}$.

A solution in glacial acetic acid becomes deep green with $\lambda_{max}=442, 645$ nm. An intense yellowish-tinged green coloration is achieved on acid clay and on bisphenol A.

EXAMPLE 14

The compound of the formula with a melting point of 67°–70° C., is obtained analogously in a 62% yield.

A solution in glacial acetic acid becomes green with $\lambda_{max}=440, 648$ nm. An intense yellowish-tinged green coloration develops on acid clay or with bisphenol A.

EXAMPLE 15

The compound of the formula of melting point 179° C., is obtained analogously in a 30% yield.

IR: 1608 cm$^{-1}$.

A solution in glacial acetic acid becomes green with $\lambda_{max}=442, 644$ nm. An intense yellowish-tinged green coloration develops on acid clay or with bisphenol A.

EXAMPLE 16

The compound of the formula

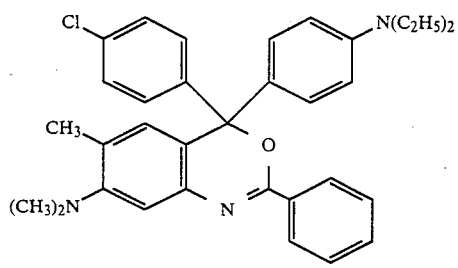

of melting point 170°–172° C. is obtained analogously in a 35% yield.

A solution in glacial acetic acid becomes black-green with $\lambda_{max}$ 450, 632 nm.

A green intense coloration develops on acid clay and with bisphenol A.

EXAMPLE 17

The compound of the formula

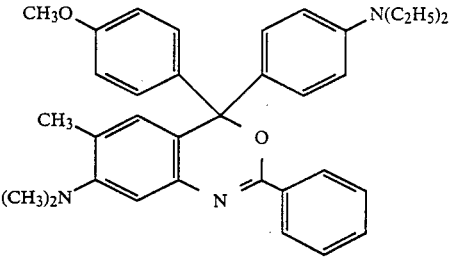

of melting point 159°–161° C. is obtained analogously in a 48% yield.

A solution in glacial acetic acid becomes black with $\lambda_{max}$ 491, 592 nm.

A black intense coloration develops on acid clay and with bisphenol A.

EXAMPLE 18

The compound of the formula

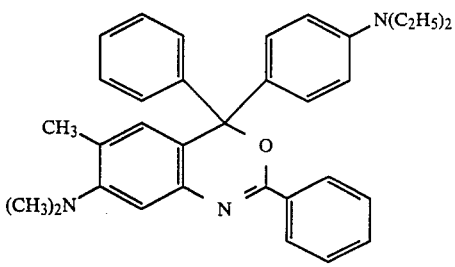

of melting point 142°–143° C. is obtained analogously in a 45% yield.

A solution in glacial acetic acid becomes green with $\lambda_{max}$ 448, 628 nm.

A dirty green coloration develops on acid clay and with bisphenol A.

The compounds of Examples 19 to 31 can be prepared analogously.

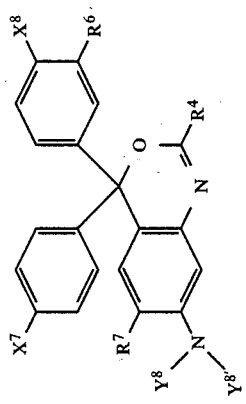

| Example | X⁷ | X⁸ | R⁶ | Y⁸ | Y⁸' | R⁷ | R⁴ | Colour shade on acid clay or with bisphenol A |
|---|---|---|---|---|---|---|---|---|
| 19 | N(CH₃)₂ | –C₆H₄–CH₃ (p-tolyl) | H | CH₃ | CH₃ | H | H | green |
| 20 | 4-methylpiperazin-1-yl | –SCH₃ | H | C₂H₅ | H | CH₃O | C₂H₅ | green |
| 21 | N(CH₂C₆H₅)₂ | C₆H₅–C(=O)–NH– | H | CH₃ | CH₃ | H | p-CH₃O-C₆H₄ | green |
| 22 | N(C₂H₄OCOCH₃)₂ | Br | CH₃ | C₂H₅ | C₂H₅ | H | p-COOCH₃-C₆H₄ | yellowish-tinged green |
| 23 | N(C₂H₅)₂ | OCH₃ | H | CH₃ | CH₃ | CH₃ | –C(CH₃)₃ | black |
| 24 | pyrrolidin-1-yl | –OCH₂C₆H₅ | CH₃ | CH₃ | CH₃ | H | o-CH₃-C₆H₄ | green |

-continued

[Structure: triphenylmethane-type compound with substituents X⁷, X⁸, R⁶, R⁷, Y⁸, Y⁸', and N=C(R⁴)–O bridge]

| Example | X⁷ | X⁸ | R⁶ | Y⁸ | Y⁸' | R⁷ | R⁴ | Colour shade on acid clay or with bisphenol A |
|---|---|---|---|---|---|---|---|---|
| 25 | 4-(N-CH₃)(OC₂H₅)-phenyl | Cl | CH₃ | CH₃ | CH₂CH₂OCH₃ | H | –CH(C₂H₅)(C₄H₉) | green |
| 26 | 4-Cl-anilino (N-H) | OC₂H₅ | H | CH₃ | C₁₈H₃₇ | H | 4-SO₂CH₃-phenyl | green |
| 27 | N-CH₃-anilino | N-CH₃-anilino | H | CH₃ | CH₃ | H | 4-CH₃-phenyl | blue |
| 28 | –OCH₃ | –N(C(CH₃)₂CH₂C(CH₃)₂C₂H₅) | –CH(CH₃)₂ | CH₃ | CH₃ | CH₃ | phenyl | bluish-tinged green |
| 29 | –N(C₂H₅)₂ | H | C₂H₅ | CH₃ | CH₃ | CH₃ | phenyl | dull green |
| 30 | –N(C₂H₅)₂ | CH₃O | H | C₂H₅ | C₂H₅ | CH₃ | phenyl | black |

-continued

| Example | $X^7$ | $X^8$ | $R^6$ | $Y^8$ | $Y^{8'}$ | $R^7$ | $R^4$ | Colour shade on acid clay or with bisphenol A |
|---|---|---|---|---|---|---|---|---|
| 31 | —N(CH$_3$)$_2$ | CH$_3$O | CH$_3$ | CH$_3$ | CH$_3$ | H | ⌬-CH$_3$ | dull green |

EXAMPLE 32

72.2 g of the ketone of the formula

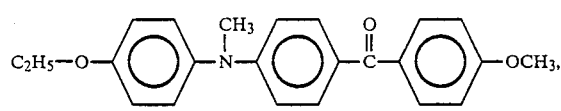

60.4 g of the amide of the formula

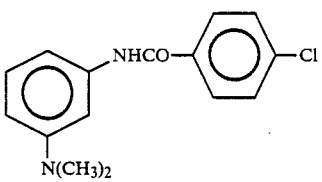

and 85.2 g of phosphorus pentoxide are introduced into 154.3 g of phosphorus oxychloride. The mixture is stirred at 80° C. for 2 days and then taken up in 200 ml of o-dichlorobenzene. The mixture is discharged onto 2 l of water at room temperature and rendered alkaline. The organic phase is separated off and the solvent is distilled off with steam. The beige crystals are filtered off with suction and recrystallised from 2-propanol.

80.3 g (65%) of the compound of the formula

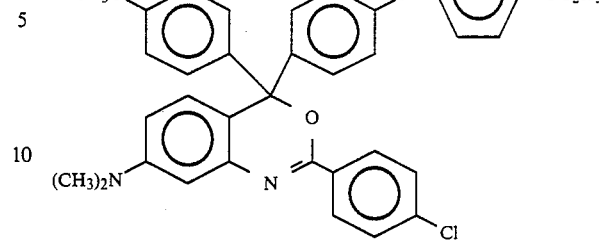

of melting point 159°–161° C. are obtained.
IR (KBr): 1605 cm$^{-1}$.

A solution in glacial acetic acid becomes green with $\lambda_{max}=492$, 636 nm. An intense dirty green coloration is achieved on acid clay and with bisphenol A.

EXAMPLE 33

The compound of the formula

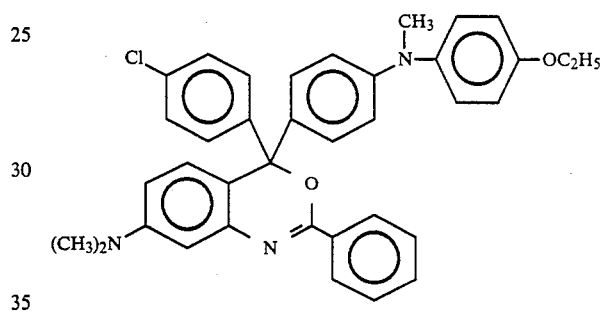

of melting point 85°–87° C. is obtained analogously in a 45% yield.

A solution in glacial acetic acid becomes green with $\lambda_{max}=455$, 658 nm. An intense yellowish-tinged green coloration is achieved on acid clay or with bisphenol A.

The compounds of Examples 34–37 are obtained analogously.

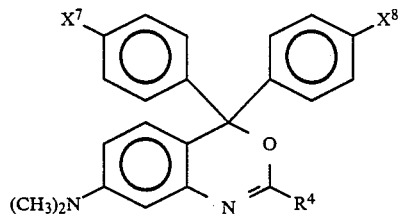

| Example | X$_7$ | X$_8$ | R$^4$ | λmax | Colour shade on acid clay or with bisphenol A |
|---|---|---|---|---|---|
| 34 | CH$_3$O | -N(CH$_3$)-C$_6$H$_4$-CN | -C$_6$H$_4$-CN | 496,632 nm | blackish blue |
| 35 | H | -N(CH$_3$)-C$_6$H$_4$-CN | -C$_6$H$_5$ | 440,652 nm | dull yellowish-tinged green. |

-continued

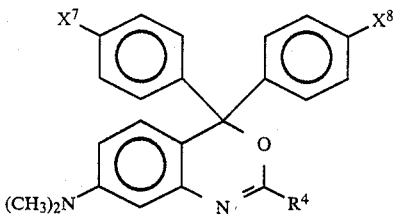

| Example | X7 | X8 | R4 | λmax | Colour shade on acid clay or with bisphenol A |
|---|---|---|---|---|---|
| 36 | CH3O | —N(CH3)(C6H5) | C6H5 | 485, 637 nm | dull bluish-tinged green |
| 37 | Cl | —N(CH3)(C6H4-CN) | C6H5 | 450, 646 nm | dull dirty green |

EXAMPLE 38

A mixture of 14.4 g of 4-chloro-4'-(diethylamino)benzophenone and 15.4 g of 1-(3-benzoylaminophenyl)-3,5,5-trimethyl-$\alpha^2$-pyrazoline in introduced into a mixture of 38.3 g of phosphorus oxychloride and 28.3 g of phosphorus pentoxide, with cooling. The mixture is then stirred at 20° to 25° C. for 66 hours and at 35° to 40° C. for 24 hours. The green melt is dissolved in 50 ml of acetonitrile and the solution is poured onto a mixture of 200 ml of chloroform and 800 ml of 10% strength sodium hydroxide solution. The chloroform phase is separated off and dried over sodium carbonate and the solvent is removed. The resulting brown resin is made to crystallise in 100 ml of methanol. The yellow powder is filtered off with suction and recrystallised from toluene. 6.9 g (24% of theory) of pale yellow crystals of melting point 235° to 238° C. and of the formula

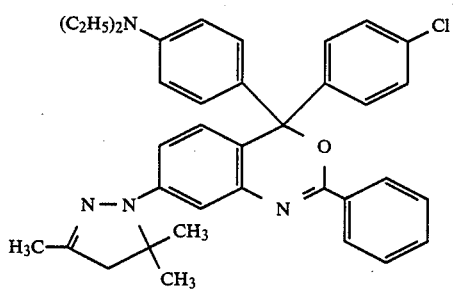

are obtained.

A solution in glacial acetic acid becomes deep green with $\lambda_{max}$=454, 674 nm. An intense yellowish-tinged green coloration is obtained on acid clay and with bisphenol A.

EXAMPLE 39

37.7 g of the leuco compound of the formula

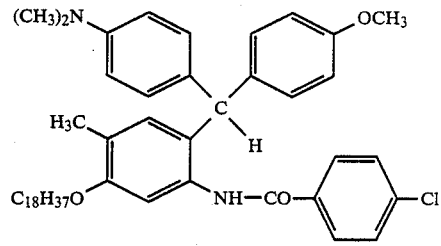

of melting point 109° to 111° C., prepared analogously to Example 1, are dissolved in 50 ml of dimethylformamide. 12.3 g of chloranil are added at 60° C. and the mixture is stirred at 65° to 70° C. for 1 hour. It is then cooled, diluted with 100 ml of dimethylformamide and decolorised with about 10 ml of 10% strength sodium hydroxide solution. After the mixture has been stirred for 3 hours, the product which has precipitated is filtered off with suction, stirred cold with 50 ml of ethanol and then boiled up again with 70 ml of ethanol and 1 ml of triethylamine. Finally, the product is filtered off with suction, washed with ethanol and dried in vacuo: 27.7 g (74% of theory) of pale beige crystalline powder of melting point 94° to 95° C. and with the formula

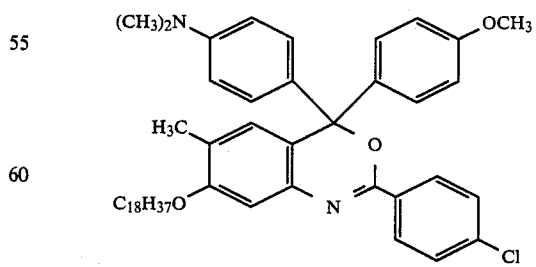

IR (KBr): 1605, 1595 cm$^{-1}$.

A solution in glacial acetic acid becomes deep claret with $\lambda_{max}$=548 nm. A deep claret coloration is likewise produced on acid clay and with bisphenol A.

EXAMPLE 40

The compound of the formula

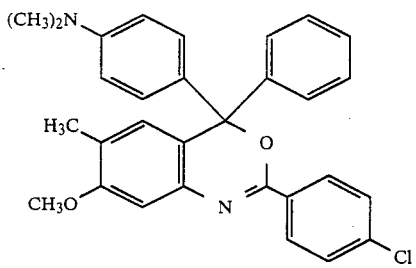

of melting point 215° to 217° C. can be prepared analogously in a 46% yield.

A solution in glacial acetic acid becomes deep red with $\lambda_{max}=511$ nm. An intense red coloration is achieved on acid clay and with bisphenol A.

EXAMPLE 41

53.6 g of phosphorus oxychloride and 29.7 g of phoshorus pentoxide are taken in an ice-bath. A mixture of 19.8 g of 4-(diethylamino)-4'-methoxy-benzophenone and 19.4 g of 3-methoxy-4-methyl-4'-chlorobenzanilide is introduced. The claret-coloured melt is stirred at 25° to 30° C. for 88 hours and then taken up in 70 ml of acetonitrile. This solution is added dropwise to 500 ml of water at 10° C. and the mixture is then stirred at 20° to 25° C. for a further hour. The colour resin deposited is decanted and dissolved in 300 ml of dimethylformamide. This solution is now added dropwise to 1 l of water and a pH of 7 to 8 is then established with 10% strength sodium hydroxide solution. The suspension is warmed to 45° C. and the pH is maintained. After cooling, the precipitate is filtered off with suction, washed with water and dried in vacuo. The yellow-beige powder is now boiled up in succession with 120 ml of 2-propanol, 50 ml of 2-propanol and 50 ml of methanol, and in each case after cooling filtered off with suction and washed, and finally dried in vacuo: 24.7 g (65% of theory) of beige crystalline powder of melting point 196° to 199° C. and with the formula

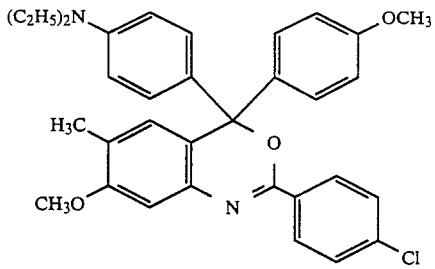

A solution in glacial acetic acid becomes deep claret with $\lambda_{max}=548$ nm. A deep claret coloration is likewise achieved on acid clay and with bisphenol A.

The compounds of Examples 42 to 52 are prepared analogously to examples 39 to 41.

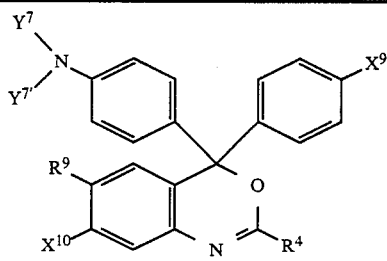

| Example | $Y^7$ | $Y^{7'}$ | $X^9$ | $X^{10}$ | $R^9$ | $R^4$ | Melting point | $\lambda max$ | Colour shade on acid clay or with bisphenol A |
|---|---|---|---|---|---|---|---|---|---|
| 42 | $C_2H_5$ | $C_2H_5$ | $CH_3O$ | $CH_3O$ | $CH_3$ | $CH_3$ | — | 540 nm | claret |
| 43 | " | " | " | " | " | $-CH(C_2H_5)(C_4H_9)$ | — | 540 nm | " |
| 44 | " | " | " | " | " | $C_6H_5$ | 209° C. | 548 nm | " |
| 45 | " | " | " | " | " | –C6H4–OCH3 | 108° C. | 549 nm | " |
| 46 | " | " | " | " | " | pyridyl | — | 548 nm | " |
| 47 | " | " | " | " | $CH_3O$ | $C_6H_5$ | 93–95° C. | 554 nm | bluish red |

-continued

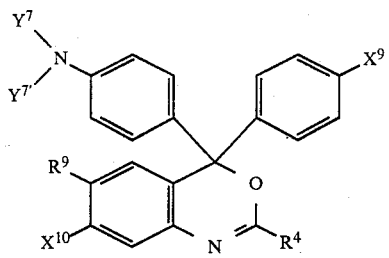

| Example | $Y^7$ | $Y^{7'}$ | $X^9$ | $X^{10}$ | $R^9$ | $R^4$ | Melting point | $\lambda$max | Colour shade on acid clay or with bisphenol A |
|---|---|---|---|---|---|---|---|---|---|
| 48 | $C_6H_5$ | $CH_3$ | $C_2H_5O$ | $C_2H_5O$ | Cl | naphthyl | | | red |
| 49 | $CH_3$ | $CH_3$ | $(C_3H_7)_2N$ | H | | $C_6H_5$-NH-$C_6H_4$-CN | | | green |
| 50 | " | $C_2H_4CN$ | $C_6H_5CONH$ | $C_6H_5O$ | $CH_3O$ | $-C(CH_3)_3$ | | | " |
| 51 | $C_2H_5$ | $C_2H_5$ | Cl | | $CH_3O$ | $CH_3$ | $-CH_2-C_6H_4-Cl$ | | red |
| 52 | " | " | $CH_3O$ | $C_2H_5O$ | $CH_3$ | phenyl | | | claret |

EXAMPLE 53

A mixture of 12.8 g of 4,4'-dimethoxy-3-methylbenzophenone and 13.7 g of 3-(dimethylamino)-4'-chlorobenzanilide is introduced into a mixture of 38.3 g of phosphorus oxychloride and 21.2 g of phosphorus pentoxide, while cooling. The melt is stirred at 20° to 25° C. for 66 hours and at 35° to 40° C. for 24 hours and then taken up in 50 ml of acetonitrile. This solution is now added dropwise to a mixture of 200 ml of chloroform and 800 ml of 10% strength sodium hydroxide solution. The chloroform phase is separated off, dired with sodium carbonate and filtered over 200 g of silica gel and the solvent is removed in vacuo. The residue is boiled up twice in 25 ml of methanol and dried: 9.9 g (39% of theory) of pale yellow powder of melting point 112° to 115° C. and with the formula

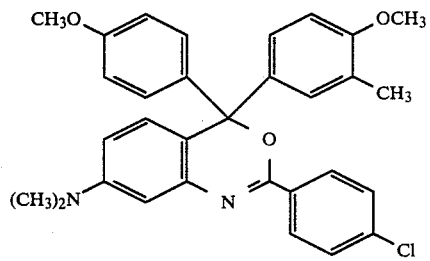

IR (KBr): 1598 cm$^{-1}$.

A solution in glacial acetic acid becomes deep violet with $\lambda_{max}$=456, 581 nm. An intense blackish violet coloration is achieved on acid clay, and a grey coloration is achieved with bisphenol A.

EXAMPLE 54

The compound of the formula

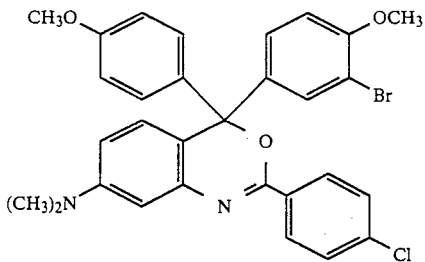

of melting point 118° to 122° C. can be prepared analogously in an 88% yield.

A solution in glacial acetic acid becomes violet with $\lambda_{max}=416$, 571 nm. A violet coloration is achieved on acid clay.

EXAMPLE 55

The compound of the formula

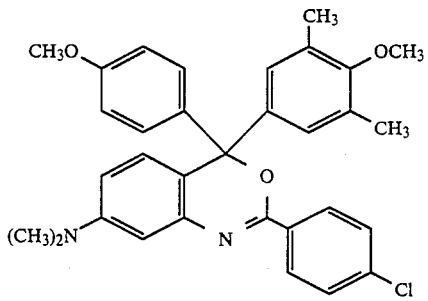

with a melting point of 215°–218° C. can be prepared analogously in a 56% yield.

A solution in glacial acetic acid becomes redviolet with $\lambda_{max}=410$, 566 nm. A red to violet coloration is achieved on acid clay and with bisphenol A.

EXAMPLE 56

The compound of the formula

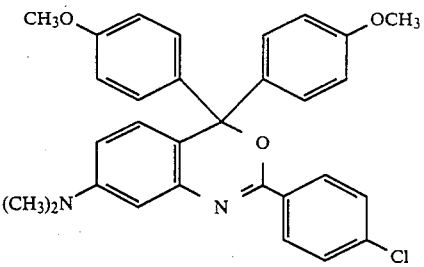

with a melting point of 179°–180° C. can be prepared analogously in a 86% yield.

A solution in glacial acetic acid becomes deep violet with $\lambda_{max}=420$, 446, 580 nm. A violet or grey coloration is achieved on acid clay or with bisphenol A.

Examples 57–66 can also be prepared analogously.

| Example | $X^7$ | $X^8$ | $R^6$ | $R^5$ | $R^8$ | $R^4$ | Colour shade on acid clay or with bisphenol A |
|---------|-------|-------|-------|-------|-------|-------|---|
| 57 | H | $C_2H_5O$ | H | $CH_3O$ | H | 4-pyridyl | red |
| 58 | " | $CH_3$ | " | " | Cl | 4-CN-phenyl | " |
| 59 | $CH_3O$ | $CH_3O$ | $CH_3$ | H | " | 4-$CH_3$-phenyl | red-violet |

-continued

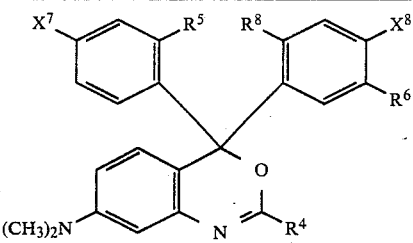

| Example | $X^7$ | $X^8$ | $R^6$ | $R^5$ | $R^8$ | $R^4$ | Colour shade on acid clay or with bisphenol A |
|---|---|---|---|---|---|---|---|
| 60 | $CH_3$ | " | Cl | " | H | 4-quinolinyl | orange |
| 61 | $C_2H_5O$ | $CH_3$ | $CH_3$ | " | $CH_3$ | 4-($COOC_2H_5$)phenyl | orange-red |
| 62 | $CH_3O$ | $CH_3O$ | H | $CH_3O$ | H | phenyl | red-violet |
| 63 | $CH_3O$ | $CH_3O$ | $CH_3O$ | H | H | phenyl | " |
| 64 | $CH_3O$ | $N(CH_3)_2$ | H | H | $NHCH_3$ | 4-Cl-phenyl | black |
| 65 | $CH_3O$ | $-N(CH_3)-C(CH_3)_2-CH_2-CH(CH_3)-$ | H | H | | phenyl | bluish-tinged green |
| 66 | $CH_3O$ | $CH_3O$ | $CH_3O$ | $CH_3O$ | H | $-C_3H_7$ | red-violet |

EXAMPLE 67

A mixture of 13.5 g of 4,4'-dimethoxy-3-methylbenzophenone and 14.0 g of 3-methoxy-4-methyl-4'-chlorobenzanilide is introduced into a mixture of 38.3 g of phosphorus oxychloride and 21.2 g of phosphorus pentoxide, while cooling. The red-orange melt is stirred at 20° to 25° C. for 48 hours and at 35° to 40° C. for 24 hours and then taken up in 35 ml of acetonitrile. The solution is added dropwise to 1 l of ice-water at 0° C. This suspension is rendered alkaline with concentrated sodium hydroxide solution, likewise at 0° C., and allowed to come to room temperature and kept alkaline. The precipitate is filtered off with suction, washed with water and, while still moist, stirred into 150 ml of methanol. After filtering off with suction, the precipitate is refluxed in 50 ml of methanol for ½ hour, with the addition of 10 ml of triethylamine, the mixture is cooled and the product is filtered off with suction, washed with methanol and dried in vacuo. 12.0 g (47% of theory) of colourless crystalline powder of melting point 173° to 177° C. and of the formula

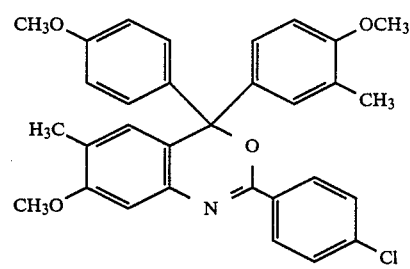

are thus obtained.

IR(KBr): 1595 cm$^{-1}$.

A solution in glacial acetic acid becomes red with $\lambda_{max}=485$ nm. A pink coloration is achieved on acid clay.

EXAMPLE 68

A mixture of 14.9 g of 4-(diethylamino)-2-ethoxybenzophenone and 13.7 g of 3-(dimethylamino)-4'-chlorobenzanilide is introduced into a mixture of 38.3 g of phosphorus oxychloride and 21.2 g of phosphorus pentoxide, while cooling. The green melt is stirred at 20° to 25° C. for 136 hours and then taken up in 50 ml of acetonitrile. This solution is added dropwise to 300 ml of water at 10° C. After 1 hour at 20° to 25° C., 45 g of sodium acetate are added to the brown solution and the mixture is extracted four times with 100 ml of toluene. Finally, the pH is brought to 7 with concentrated sodium hydroxide solution and the colour resin deposited is decanted and dissolved in 200 ml of dimethylformamide. This solution is added dropwise to 1 l of water and the pH is brought to 7 with 10% strength sodium hydroxide solution. The product which flocculates out is filtered off with suction, washed with water and dried in vacuo. The yellow-green powder is stirred in 100 ml of 2-propanol for 1 hour and boiled up and, after cooling, filtered off with suction, washed with 2-propanol and dried in vacuo: 13.8 g (50% of theory) of beige crystals of melting point 154° to 157° C. and with the formula

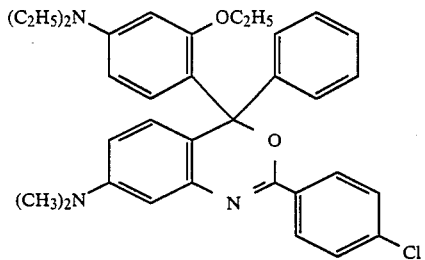

A solution in glacial acetic acid becomes yellowish-tinged green with $\lambda_{max}=443, 656$ nm. An intense yellowish-tinged green coloration is achieved on acid clay and with bisphenol A.

EXAMPLE 69

The compound of the formula

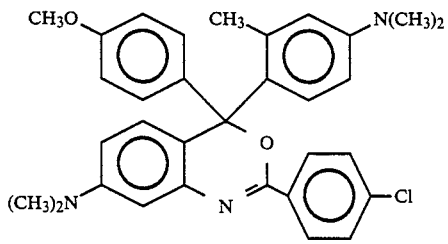

of melting point 230°–233° C. is obtained analogously in a 58% yield.

A solution in glacial acetic acid becomes green with $\lambda_{max}=490, 643$ nm.

An intense grey-green coloration is achieved on acid clay and on bisphenol A.

EXAMPLE 70

The compound of the formula

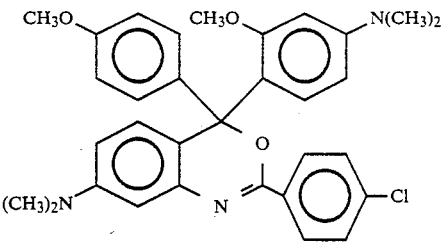

of melting point 182° C. can be prepared analogously in a 31% yield.

A solution in glacial acetic acid becomes green with $\lambda_{max}=478, 642$ nm. An intense yellowish-tinged grey-green coloration is achieved on acid clay and with bisphenol A.

EXAMPLE 71

The compound of the formula

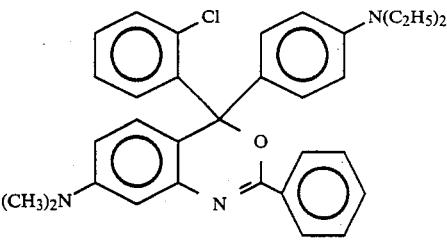

of melting point 141°–142° C. (decomposition) is obtained analogously in a 46% yield.

A solution in glacial acetic acid becomes green with $\lambda_{max}=426, 662$ nm. IR: 1608 cm$^1$.

An intense luminous-green coloration is achieved on acid clay and with bisphenol A.

EXAMPLE 72

13.6 g of 4-methoxy-benzaldehyde and 54.8 g of 3-(dimethylamino)-4'-chloro-benzanilide are refluxed in 150 ml of ethanol with 15 ml of concentrated hydrochloric acid for 3 hours. After cooling, the mixture is rendered alkaline with 30% strength methanolic sodium methylate solution and filtered and the filtrate is added dropwise to 1.5 l of ice-water. The suspension is filtered with suction and the residue is washed with acetone and, while still moist, then refluxed in 100 ml of acetone for 30 minutes, the mixture is cooled and filtered with suction and the product is washed with acetone and dried in vacuo. 45.4 g (68% of theory) of colourless crystals of melting point 220° to 222° C. and of the formula

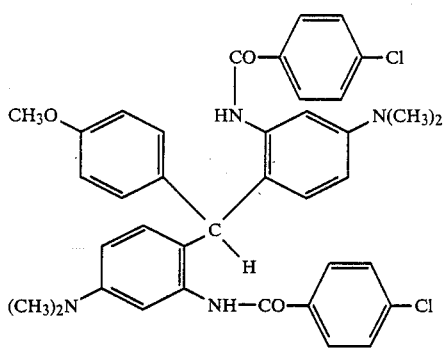

are obtained.

8.2 g of chloranil are added to 20 g of this leuco compound in 30 ml of dimethylformamide at 60° C. and the mixture is stirred at 65° to 70° C. for 1 hour. After cooling, it is diluted with 30 ml of methanol and the mixture is added dropwise to 500 ml of water. The mixture is decolorised with 10% strength sodium hydroxide solution and filtered with suction. While still moist, the residue is boiled up in methanol, the pH is brought to 9 with 10% strength sodium hydroxide solution, the mixture is stirred cold and filtered with suction and the residue is washed with methanol/water 1/1. The product is dried in vacuo: 18.3 g (92% of theory) of pale grey crystalline powder of melting point 189° to 192° C. and with the formula

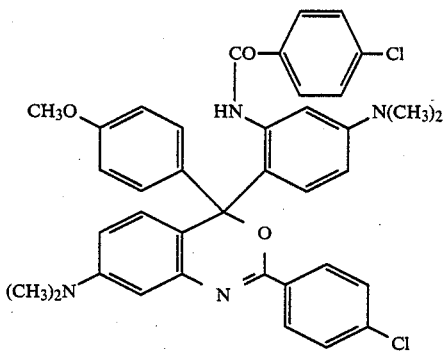

A solution in glacial acetic acid becomes black with $\lambda_{max}$=508,660 nm. A black colour shade is likewise developed on acid clay and with bisphenol A.

EXAMPLE 73

The compound of the formula

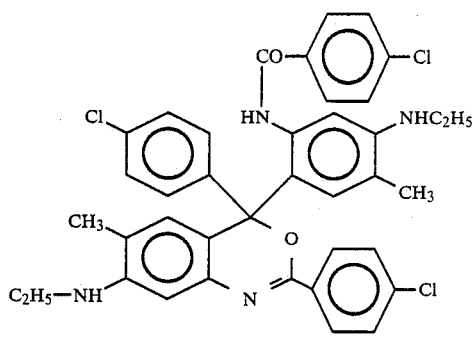

of melting point 180°–185° C. can be prepared analogously in a 78% yield.

A solution in glacial acetic acid becomes green with $\lambda_{max}$=452,672 nm.

A dirty green coloration is achieved on acid clay and with bisphenol A.

EXAMPLE 74

The compound of the formula

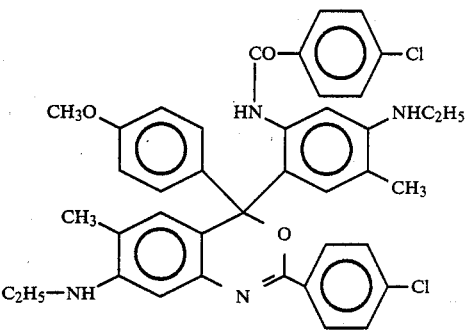

of melting point 167°–170° C. is obtained analogously in a 22% yield.

A solution in glacial acetic acid becomes black with $\lambda_{max}$=501,648 nm.

An intense black coloration is likewise achieved on acid clay and on bisphenol A.

Examples 75–82 can be prepared analogously.

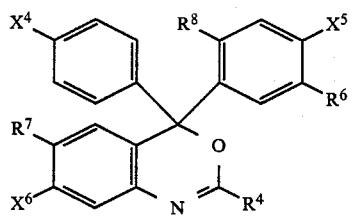

| Example | $X^4$ | $X^5$ | $X^6$ | $R^6$ | $R^7$ | $R^8$ | $R^4$ | Colour shade on acid clay or with bisphenol A |
|---------|-------|-------|-------|-------|-------|-------|-------|-----------------------------------------------|
| 75 | $OC_2H_5$ | $-N(CH_3)_2$ | $-N(CH_3)_2$ | H | H | $NHCOR^4$ | ―⟨⟩―$C(CH_3)_3$ | black |

-continued

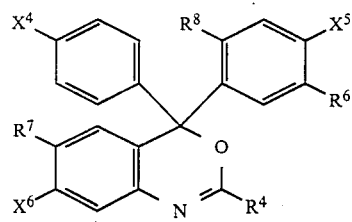

| Example | $X^4$ | $X^5$ | $X^6$ | $R^6$ | $R^7$ | $R^8$ | $R^4$ | Colour shade on acid clay or with bisphenol A |
|---|---|---|---|---|---|---|---|---|
| 76 | Cl | $-N(C_2H_5)_2$ | $-N(C_2H_5)_2$ | " | " | " | phenyl | green |
| 77 | $-N(CH_3)_2$ | $-OCH_3$ | $-OCH_3$ | $CH_3$ | $CH_3$ | " | $-C_2H_5$ | red |
| 78 | $CH_3$ | $-N(CH_3)_2$ | $-N(CH_3)_2$ | H | H | " | $-C_6H_4-COOC_2H_5$ | green |
| 79 | $OCH_3$ | $N(C_2H_5)_2$ | $N(CH_3)_2$ | H | H | $NHSO_2CH_3$ | phenyl | black |
| 80 | Cl | $N(C_3H_7)_2$ | $N(CH_3)_2$ | H | H | $NHSO_2CH_3$ | phenyl | green |
| 81 | H | $N(CH_3)_2$ | $N(CH_3)_2$ | H | H | succinimido | $-C_6H_4-CF_3$ | green |
| 82 | $OCH_3$ | $N(CH_3)_2$ | $N(CH_3)_2$ | $CH_3$ | $CH_3$ | $NHCOR^4$ | phenyl | black |

EXAMPLE 83

8.06 g of sodium boranate are added to 28.0 g of the ketone of the formula

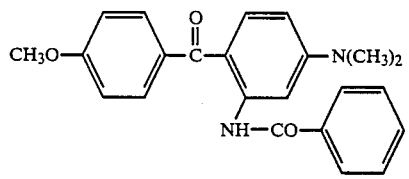

of melting point 178° to 179° C. obtained analogously to A. Kliegl, Ber. Dtschen Chem. Ges. 39, 1266 (1906), in 400 ml of ethanol and the components are stirred in suspension at 40° C. for 24 hours. The suspension is then cooled, 57 ml of acetone are added and, after subsequent stirring for 1 hour, the solid is filtered off with suction and dried in vacuo. Then the toluol and catalytic amounts of acetic acid are added and the water and subsequently the solvent are distilled off. 23.0 g (86% of theory) of pale yellowish crystals of melting point 115°–118° C. and with the formula

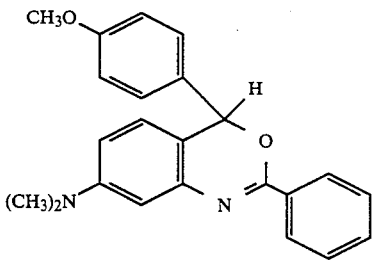

are obtained.

A solution in glacial acetic acid becomes orange-red with $\lambda_{max}=484$ nm. An orange coloration is achieved on acid clay.

EXAMPLE 84

7.4 g of the leuco compound of the formula

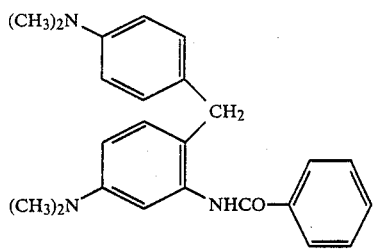

prepared according to German Patent Specification No. 79,250, are stirred in 60 ml of 80 percent strength acetic acid and 9 g of concentrated hydrochloric acid with 15.4 ml of a 31 percent strength aqueous lead dioxide suspension at 30°–35° C. for 30 minutes. 14 ml of 20 percent strength sulphuric acid are then added, the mixture is filtered and the pH is brought to 1.9. The precipitate is filtered off with suction and discarded. The pH is then brought to 3.4 and the mixture is filtered with suction. The product is boiled up in ethanol and filtered off with suction:

3.1 g (42%) of beige crystals of the formula

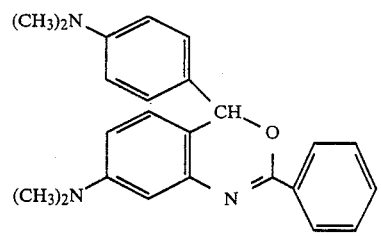

A solution in glacial acetic acid becomes blue with $\lambda_{max} = 605$ nm.

An intense blue coloration is likewise achieved on acid clay and with bisphenol A.

The compounds of Examples 85–90 are obtained analogously.

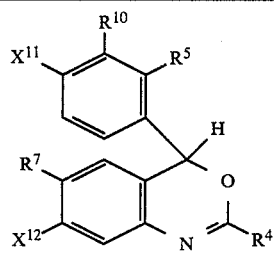

| Example | $X^{11}$ | $X^{12}$ | $R^5$ | $R^7$ | $R^{10}$ | $R^4$ | Colour shade on acid clay |
|---|---|---|---|---|---|---|---|
| 85 | $C_2H_5O$ | $N(CH_3)_2$ | Cl | H | H | phenyl | orange-red |
| 86 | $N(C_2H_5)_2$ | $CH_3O$ | H | $CH_3$ | " | $CH_3$ | " |
| 87 | $-OCH_2-$phenyl | $-N(morpholine)O$ | " | H | $CH_3$ | 3-methylphenyl | " |
| 88 | $N(CH_3)_2$ | $N(CH_3)_2$ | " | $CH_3$ | H | phenyl | blue |
| 89 | NH$C_2H_5$ | NH$C_2H_5$ | " | $CH_3$ | $CH_3$ | 4-chlorophenyl | " |
| 90 | $N(CH_3)_2$ | $N(CH_3)_2$ | NHCO-phenyl | H | H | phenyl | turquoise |

EXAMPLE 91

PREPARATION OF A PRESSURE-SENSITIVE COPYING PAPER

A solution of 3 g of the 3,1-benzoxazine compound of Example 1 in 80 g of diisopropylnaphthalene and 17 g of kerosene is microencapsulated with gelatine and gum arabic be coacervation in a manner which is known per se, the microcapsules are mixed with starch solution and the mixture is brushed onto a sheet of paper. The front side of a second sheet of paper is coated with acid-activated bentonite, as the colour developer. The first sheet and the sheet coated with colour developer are placed on top of one another with the coatings adjacent. By writing manually or with a typewriter on the first sheet, pressure is exerted and an intense turquoise copy which is excellently fast to light develops on the sheet coated with the developer.

EXAMPLE 92

1 g of the 3,1-benzoxazine compound of Example 72 is dissolved in 17 g of toluene. 12 g of polyvinyl acetate, 8 g of calcium carbonate and 2 g of titanium dioxide are added to this solution, with stirring. The resulting suspension is diluted with toluene in a weight ratio of 1/1 and spread onto a sheet of paper with a 10 μm doctor blade. A second sheet of paper, the underside of which is coated with a mixture—consisting of 1 part of zinc chloride—in an application weight of 3 g/m$^2$, is placed on this sheet of paper. By writing manually or with a typewriter on the upper sheet, pressure is exerted and an intense black colour which is fast to light develops on the sheet coated with the colour-forming agent.

EXAMPLE 93

The procedure is as in Example 91, except that a mixture of 1.5 g of the compound of Example 68 and 1.5 g of the compound of Example 41 is employed. A coated sheet which gives a black copy which is excellently fast to light is thus obtained.

The mixtures of Examples 94 to 104 are prepared analogously:

| Example | Compound of Example | Amount | Compound of Example | Amount | Colour Shade |
|---|---|---|---|---|---|
| 94 | 12 | 1,8 g | 39 | 1,2 g | black |
| 95 | 10 | 1,0 g | 47 | 2,0 g | black |
| 96 | 10 | 1,5 g | 40 | 1,5 g | black |
| 97 | 12 | 1,5 g | 40 | 1,5 g | black |
| 98 | 35 | 1,5 g | 41 | 1,5 g | black |
| 99 | 32 | 1,0 g | 53 | 2,0 g | black |
| 100 | 71 | 1,2 g | 41 | 1,8 g | black |
| 101 | 36 | 1,5 g | 53 | 1,5 g | black |
| 102 | 16 | 1,8 g | 52 | 1,2 g | black |
| 103 | 17 | 2,4 g | 47 | 0,6 g | reddish black |
| 104 | 18 | 1,5 g | 56 | 1,5 g | black |

PREPARATION OF HEAT-SENSITIVE RECORDING MATERIALS

EXAMPLE 105

32 g of 4,4'-isopropylidene-diphenol (bisphenol A), 3.8 g of the distearylamide of ethylenediamine, 89 g of kaolin, 20 g of a polyvinyl alcohol hydrolysed to the extent of 88% and 55 ml of water are ground in a ball mill until the particle size is about 5 μm. 6 g of the 3,1-benzoxazine compound of Example 11, 3 g of a polyvinyl alcohol hydrolysed to the extent of 88% and 60 ml of water are ground to a particle size of about 3 μm in a second ball mill. The two dispersions are brought together and brushed onto paper with a dry application weight of 5.5 g/m$^2$. By touching the paper with a heated ball-point pen, an intense green coloration which has good fastness to light and sublimation is obtained.

EXAMPLE 106

2.7 g of the 3,1-benzoxazine compound of Example 44, 24 g of N-phenyl-N'-(1-hydroxy-2,2,2-trichloroethyl)-urea, 16 g of stearic acid, 59 g of a polyvinyl alcohol hydrolysed to the extent of 88% and 58 ml of water are ground in a ball mill until the particle size is 2 to 5 μm. This suspension is brushed onto a sheet of paper with a dry application weight of 5.5 g/m$^2$. By touching the paper with a heated ball-point pen, an intense claret colour which is fast to light is obtained.

EXAMPLE 107

In accordance with German Offenlegungsschrift No. 3,337,296, 40 g of a finely powdered polyacrylonitrile polymer, prepared from 94% of acrylonitrile, 0.5% of methallylsulphonic acid and 5.5% of methyl acrylate, are ground with 225 g of an 8% strength aqueous polyvinyl alcohol solution, with the addition of 1.3 g of distearyl phosphate, in a ball mill. A second dispersion is prepared from 1 g of the benzoxazine compound of Example 53 and 55 g of an 8% strength aqueous polyvinyl alcohol solution. The dispersion of the colour-forming agent is mixed with that of the acceptor in a ratio of 1/10 and the mixture is applied to cellulose paper by means of a doctor blade and dried so that an application weight of 6 to 7 g/m$^2$ is obtained. The paper can be written on with writing materials, such as, for example, a ball-point pen. It is insensitive to high pressure. When the paper is touched with a heated pen, a clear, sharp, shadow-free black script is obtained. The light-fastness of the coloration is excellent.

I claim:
1. A chromogenic 3,1-benzoxazine of the formula

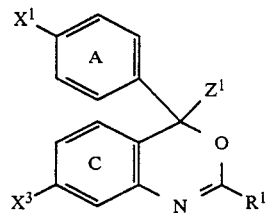

wherein
Z$^1$ denotes hydrogen, alkyl, cycloalkyl or

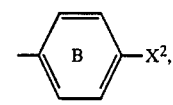

R$^1$ denotes hydrogen, alkyl, cycloalkyl, aralkyl, aryl, heterocyclic-alkylene or a heterocyclic radical,
X$^1$, X$^2$ and X$^3$ independently of one another denote hydrogen, halogen, alkyl, cycloalkyl, aryl, alkanoylamino, aroylamino, a heterocyclic radical, NY$^1$Y$^2$, OY$^3$ or SY$^3$, at least one of the radicals X$^1$, X$^2$ or X$^3$ representing NY$^1$Y$^2$,
Y$^1$, Y$^2$ and Y$^3$ independently of one another denote hydrogen, alkyl, cycloalkyl, aralkyl, aryl or a heterocyclic radical or the remaining members of a 5-membered or 6-membered ring which extends to one of the benzene-C atoms in the o-position and optionally contains further hetero-atoms, or $Y^1+Y^2$ denote the remaining members of a 5-membered or 6-membered ring which optionally contains further hetero-atoms, said heterocyclic radical being selected from the group consisting of pyridyl, pyrimidyl, pyrazinyl, triazinyl, imidazolyl, oxazolyl, thiazolyl, triazolyl, thiadiazolyl, tetrazolyl, and benzofused, partially hydrogenated or completely hydrogenated derivatives thereof, and said heterocyclic-alkylene being the ring or ring systems recited above for said heterocyclic radical, which is linked on via methylene or ethylene, and wherein the rings A, B and C and the radicals mentioned can carry non-ionic radicals which are customary in dyestuff chemistry or which in the case of rings A, B and C can be benzo fused and wherein, if the rings A and B, do not carry further substitutents or fused-on systems and if $X^3$ represents hydrogen, dialkylamino or diaralkylamino $X^1$ and $X^2$ are not simultaneously, dialkylamino or if $R^1$ represents

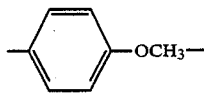

$X^1$ and $X^2$ are not simultaneously methoxy, or if $Z^1$ represents hydrogen $X^1$ is not $C_1-C_3$-alkoxy.

2. Chromogenic 3,1-benzoxazines of the formula

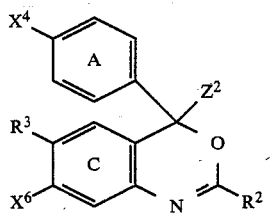

wherein one of the radicals $X^6$ or $R^3$ denotes $NY^4Y^5$, $OY^6$ or $SY^6$ and the other denotes hydrogen, $C_1-C_{18}$-alkyl, which can be substituted by fluorine, chlorine, bromine, $C_1-C_8$-alkoxy, cyano and/or $C_1-C_{18}$-alkoxycarbonyl, cyclohexyl, or benzyl, phenyl, biphenylyl or naphthyl radicals which can be substituted by chlorine, $C_1-C_8$-alkyl, $C_1-C_8$-alkoxy, cyano, $C_1-C_4$-alkoxycarbonyl and/or $C_1-C_4$-alkanoylamino, or $C_1-C_8$-alkanoylamino or benzoylamino, which can be substituted by chlorine, $C_1-C_4$-alkyl and/or $C_1-C_4$-alkoxy, $Z^2$ denotes hydrogen, $C_1-C_8$-alkyl, cyclohexyl or

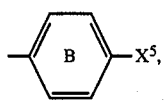

$R^2$ denotes hydrogen, $C_1-C_{18}$-alkyl which optionally carries fluorine, chlorine, bromine, $C_1-C_8$-alkoxy, cyano or $C_1-C_{18}$-alkoxycarbonyl, cyclohexyl, or benzyl, phenyl, biphenylyl, terphenylyl, naphthyl, picolyl, pyridyl, quinolyl, pyrimidyl, pyrazinyl, triazinyl, triazolyl, triazolylmethyl, thiadiazolyl, tetrazolyl, indolyl or optionally benzofused imidazole, oxazole or thiazole radicals which optionally carry fluorine, chlorine, bromine, nitro, $C_1-C_{18}$-alkyl, $C_1-C_{18}$-alkoxy, $C_1-C_{18}$-alkylthio, $C_1-C_{18}$-mono- or dialkylamino, $C_1-C_{18}$-alkylsulphonyl, cyano, $C_1-C_{18}$-alkoxycarbonyl and/or $C_1-C_{18}$-alkanoylamino, $X^4$ and $X^5$ independently of one another denote hydrogen, fluorine, chlorine, bromine or $C_1-C_{18}$-alkyl, $C_1-C_{18}$-alkyl which is optionally substituted by fluorine, chlorine, nitro, hydroxyl, $C_1-C_8$-alkoxy, $C_1-C_8$-alkylthio, cyano, $C_1-C_8$-alkoxycarbonyl, $C_1-C_8$-alkanoyloxy, amino and/or mono- or di-$C_1-C_4$-alkylamino, phenyl which is optionally substituted by chlorine and/or $C_1-C_{12}$-alkyl, $C_1-C_{12}$-alkanoylamino, benzoylamino which is optionally substituted by chlorine and/or $C_1-C_{12}$-alklyl, indolyl or piperdyl radicals which are optionally substituted by $C_1-C_4$-alklyl, $C_1-C_4$-alkoxy, chlorine and/or phenyl, $NY^4Y^5$, $OY^6$ or $SY^6$, but wherein at most two of the radicals $X^4$, $X^5$ and $X^6$ are $NY^4Y^5$, $Y^4$, $Y^5$ and $Y^6$ independently of one another denote hydrogen, $C_1-C_{18}$-alkyl which is optionally substituted by chlorine, hydroxyl, di-$C_1-C_4$-alkylamino, cyano, $C_1-C_4$-alkoxycarbonyl, $C_1-C_4$-alkoxycarbonyloxy, $C_1-C_4$-alkanoyloxy or $C_1-C_4$-alkoxy, cyclohexyl or phenyl or benzyl, which can be substituted by chlorine, $C_1-C_{12}$-alkyl or $C_1-C_{12}$-alkoxy, piperidyl which is optionally substituted by $C_1-C_4$-alkyl, or members which, together with the N or O to which they are bonded and one of the rings A, B or C, are necessary to complete a ring system of the following formula

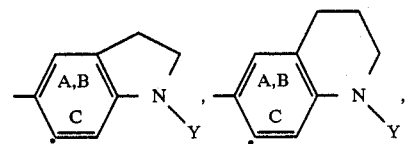

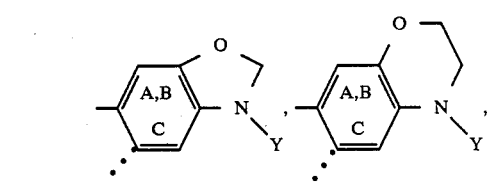

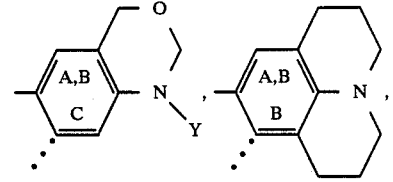

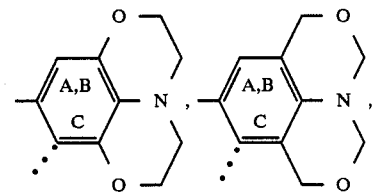

-continued

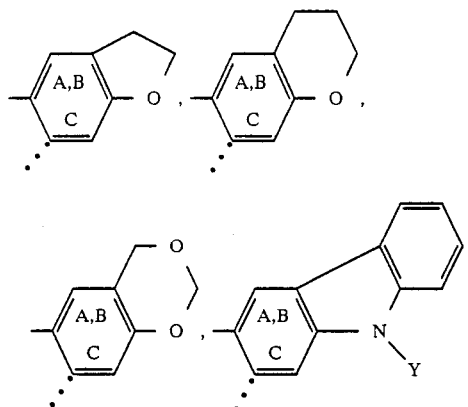

wherein
the broken line denotes further fusing-on in the case of ring C,

Y represents hydrogen, $C_1$- to $C_{18}$-alkyl, which can be substituted by chlorine, cyano, $C_1$- to $C_4$-alkoxycarbonyl or $C_1$- to $C_4$-alkoxy, cyclohexyl, or phenyl or benzyl, which can be substituted by chlorine, $C_1$- to $C_{12}$-alkyl or $C_1$- to $C_{12}$-alkoxy, the saturated ring part can carry up to 4 radicals from the group comprising chlorine, $C_1$- to $C_4$-alkyl, $C_1$- to $C_4$-alkoxy and phenyl, the rings A, B and C can be substituted by chlorine, $C_1$-$C_4$-alkyl, $C_1$-$C_4$-alkoxy, phenoxy or phenylamino which is optionally substituted by chlorine, $C_1$-$C_4$-alkyl or $C_1$-$C_4$-alkoxy and/or $C_1$-$C_4$-alkanoylamino or benzo-fused, or $NY^4Y^5$ denotes a pyrrolo, pyrrolidino, piperidino, pipecolino, pyrazino, morpholino, pyrazolo or pyrazolino radical which is optionally substituted by chlorine, $C_1$-$C_4$-alkyl or aryl.

3. Chromogenic 3,1-benzoxazines of the formula

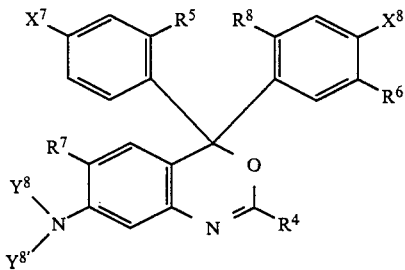

wherein
$X^8$ denotes hydrogen, chlorine, bromine, $C_1$-$C_{18}$-alkyl which is optionally substituted by chlorine and/or $C_1$-$C_4$-alkoxy, phenyl which is optionally substituted by chlorine and/or $C_1$-$C_4$-alkyl, $C_1$-$C_4$-alkanoylamino, benzoylamino which is optionally substituted by chlorine and/or $C_1$-$C_4$-alkyl, indolyl or piperidyl radicals which are optionally substituted by methyl, ethyl, methoxy, chlorine and/or phenyl, $OY^9$ or $SY^9$, $X^7$ denotes $NY^7Y^{7'}$ or independently has the meaning of $X^8$, $R^4$ denotes hydrogen, $C_1$-$C_{18}$-alkyl which optionally carries fluorine, chlorine or $C_1$-$C_4$-alkoxy, cyclohexyl, benzyl which optionally carries chlorine and/or $C_1$-$C_{18}$-alkyl, or phenyl, biphenylyl, naphthyl, picolyl, pyridyl, quinolyl, pyrimidyl, pyrazinyl, triazolyl, thiadiazolyl, indolyl or optionally benzo-fused imidazole, oxazole or thiazole radicals which optionally carry chlorine, bromine, nitro, $C_1$-$C_8$-alkyl, $C_1$-$C_8$-alkoxy, $C_1$-$C_8$-alkylthio, $C_1$-$C_8$-dialkylamino, $C_1$-$C_8$-alkylsulphonyl, cyano, $C_1$-$C_8$-alkoxycarbonyl and/or $C_1$-$C_8$-alkanoylamino, $R^5$ and $R^7$ independently of one another denote hydrogen, chlorine, bromine, $C_1$-$C_4$-alkyl, $C_1$-$C_4$-alkoxy, $C_1$-$C_4$-alkylthio, amino, $C_1$-$C_4$-mono-or dialkylamino, $C_1$-$C_4$-alkanoylamino, or $C_1$-$C_4$-alkylsulphonylamino, or benzoylamino, anilino or N-$C_1$-$C_4$-alkylanilino radicals which are optionally substituted by methyl, methoxy, ethoxy or chlorine, $R^6$ and $R^8$ independently of one another denote hydrogen, chlorine, bromine, $C_1$-$C_4$-alkyl, $C_1$-$C_4$-alkoxy, $C_1$-$C_4$-alkylthio, amino, $C_1$-$C_4$-alkanoylamino, or $C_1$-$C_4$-alkylsulphonylamino, or benzoylamino, anilino or N-$C_1$-$C_4$-alkylanilino radicals which are optionally substituted by methyl, methoxy, ethoxy or chlorine, $Y^7$ to $Y^9$ independently of one another denote $C_1$-$C_8$-alkyl which is optionally substituted by chlorine, cyano, methoxycarbonyl, methoxycarbonyloxy, acetyloxy, hydroxyl, methoxy, ethoxy or dimethylamino, cyclohexyl, benzyl, phenyl, which can be substituted by chlorine, cyano, methyl, ehtyl, methoxy or ethoxy, or 2,2,6,6-tetramethyl-or 1,2,2,6,6-pentamethyl-piperidin-4-yl, $Y^{7'}$ and $Y^{8'}$ denote hydrogen or have the meaning of $Y^7$ or $Y^8$ respectively, or $NY^7Y^{7'}$ and $NY^8Y^{8'}$ independently of one another represent a pyrrolidino, piperidino, piperazino, morpholino or pyrazolino radical which is substituted by $C_1$-$C_4$-alkyl and/or phenyl, which can also carry chlorine, methyl, methoxy, ethoxy or cyano.

4. Chromogenic 3,1-benzoxazines of the formula

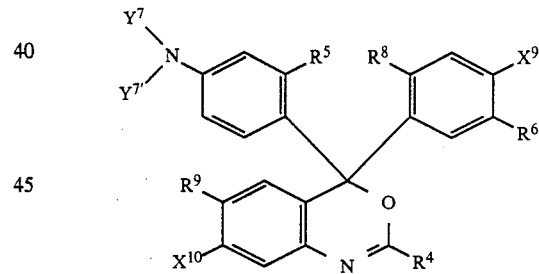

wherein
$X^9$ denotes hydrogen, chlorine, bromine, $C_1$-$C_{18}$-alkyl which is optionally substituted by chlorine and/or $C_1$-$C_4$-alkoxy, phenyl which is optionally substituted by chlorine and/or $C_1$-$C_4$-alkyl, $C_1$-$C_4$-alkanoylamino, benzoylamino which is optionally substituted by chlorine and/or $C_1$-$C_4$-alkyl, indolyl or piperidyl radicals which are optionally substituted by methyl, ethyl, methoxy, chlorine and/or phenyl, $NY^{10}Y^{10'}$, $OY^9$ or $SY^9$, $X^{10}$ denotes $OY^{11}$ or $SY^{11}$ and $R^9$ denotes hydrogen, chlorine, bromine, $C_1$-$C_4$-alkyl, $C_1$-$C_4$-alkoxy, $C_1$-$C_4$-alkylthio, $C_1$-$C_4$-alkanoylamino, benzoylamino or $C_1$-$C_4$-alkylsulphonyl-amino, or $X^{10}$ denotes hydrogen, chlorine, bromine, $C_1$-$C_{18}$-alkyl which is optionally substituted by chlorine and/or $C_1$-$C_4$-alkoxy, phenyl which is optionally substituted by chlorine and/or $C_1$-$C_4$-alkyl, C$_1$–C$_4$-alkanoylamino, benzoylamino which is optionally substituted by chlorine and/or C$_1$–C$_4$-alkyl, or indolyl or piperidyl radicals which are optionally substituted by methyl, ethyl, methoxy, chlorine and/or phenyl and R$^9$ denotes C$_1$–C$_4$-alkoxy, C$_1$–C$_4$-alkylthio, amino or C$_1$–C$_4$-mono-or dialkylamino, or anilino or N-C$_1$–C$_4$-alkylanilino which is optionally substituted by methyl, methoxy, ethoxy or chlorine, R$^4$ denotes hydrogen, C$_1$–C$_{18}$-alkyl which optionally carries fluorine, chlorine or C$_1$–C$_4$-alkoxy, cyclohexyl, benzyl which optionally carries chlorine and/or C$_1$–C$_{18}$-alkyl, or phenyl, biphenylyl, naphthyl, picolyl, pyridyl, quinolyl, pyrimidyl, pyrazinyl, triazolyl, thiadiazolyl, indolyl or optionally benzo-fused imidazole, oxazole or thiazole radicals which optionally carry chlorine, bromine, nitro, C$_1$–C$_8$-alkyl, C$_1$–C$_8$-alkoxy, C$_1$–C$_8$-alkylthio, C$_1$–C$_8$-dialkylamino, C$_1$–C$_8$-alkylsulphonyl, cyano, C$_1$–C$_8$-alkoxycarbonyl and/or C$_1$–C$_8$-alkanoylamino, R$^5$ denotes hydrogen, chlorine, bromine, C$_1$–C$_4$-alkyl, C$_1$–C$_4$-alkoxy, C$_1$–C$_4$-alkylthio, amino, C$_1$–C$_4$-mono- or dialkylamino, C$_1$–C$_4$-alkanoylamino, or C$_1$–C$_4$-alkylsulphonylamino, or benzoylamino, anilino or N-C$_1$–C$_4$-alkylanilino radicals which are optionally substituted by methyl, methoxy, ethoxy or chlorine, R$^6$ and R$^8$ independently of one another denote hydrogen, chlorine, bromine, C$_1$–C$_4$-alkyl, C$_1$–C$_4$-alkoxy, C$_1$–C$_4$-alkylthio, C$_1$–C$_4$-alkanoylamino, or C$_1$–C$_4$-alklsulphonylamino, or benzoylamino, anilino or N-C$_1$–C$_4$-alkylanilino radicals which are optionally substituted by methyl, methoxy, ethoxy or chlorine, Y$^7$ and Y$^9$ to Y$^{11}$ independently of one another denote C$_1$–C$_8$-alkyl which is optionally substituted by chlorine, cyano, methoxycarbonyl, methoxycarbonyloxy, acetyloxy, hydroxyl, methoxy, ethoxy or dimethylamino, cyclohexyl, benzyl, phenyl, which can be substituted by chlorine, cyano, methyl, ethyl, methoxy or ethoxy, or 2,2,6,6-tetramethyl or 1,2,2,6,6-pentamethyl-piperidin-4-yl, Y$^{7'}$ and Y$^{10'}$ denote hydrogen or have the meaning of Y$^7$ or Y$^{10}$, or NY$^7$Y$^{7'}$ and NY$^{10}$Y$^{10'}$ independently of one another represents a pyrrolidino, piperidino, piperazino, morpholino or pyrazolino radical which is substituted by C$_1$–C$_4$-alkyl and/or phenyl, which can also carry chlorine, methyl, methoxy, ethoxy or cyano.

5. Chromogenic 3,1-benzoxazines of the formula

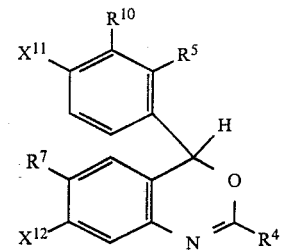

wherein

X$^{11}$ and X$^{12}$ denote NY$^{12}$Y$^{12'}$, OY$^{13}$ or SY$^{13}$,

R$^4$ denotes hydrogen, C$_1$–C$_{18}$-alkyl which optionally carries fluorine, chlorine or C$_1$–C$_4$-alkoxy, cyclohexyl, benzyl which optionally carries chlorine and/or C$_1$–C$_{18}$-alkyl, or phenyl, biphenylyl, naphthyl, picolyl, pyridyl, quinolyl, pyrimidyl, pyrazinyl, triazolyl, thiadiazolyl, indolyl or optionally benzo-fused imidazole, oxazole or thiazole radicals which optionally carry chlorine, bromine, nitro, C$_1$–C$_8$-alkyl, C$_1$–C$_8$-alkoxy, C$_1$–C$_8$-alkylthio, C$_1$–C$_8$-dialkylamino, C$_1$–C$_8$-alkylsulphonyl, cyano, C$_1$–C$_8$-alkoxycarbonyl and/or C$_1$–C$_8$-alkanoylamino, R$^5$ and R$^7$ independently of one another denote hydrogen, chlorine, bromine, C$_1$–C$_4$-alkyl, C$_1$–C$_4$-alkoxy, C$_1$–C$_4$-alkylthio, amino, C$_1$–C$_4$-mono-or dialkylamino, C$_1$–C$_4$-alkanoylamino, or C$_1$–C$_4$-alkylsulphonylamino, or benzoylamino, anilino or N-C$_1$–C$_4$-alkylanilino radicals which are optionally substituted by methyl, methoxy, ethoxy or chlorine, R$^{10}$ denotes hydrogen, chlorine, bromine, C$_1$–C$_4$-alkyl, C$_1$–C$_4$-alkoxy, C$_1$–C$_4$-alkylthio, C$_1$–C$_4$-alkanoylamino, or C$_1$–C$_4$-alkylsulphonylamino, or benzoylamino, anilino or N-C$_1$–C$_4$-alkylanilino radicals which are optionally substituted by methyl, methoxy, ethoxy or chlorine, Y$^{12}$ and Y$^{13}$ independently of one another denote C$_1$–C$_8$-alkyl which is optionally substituted by chlorine, cyano, methoxycarbonyl, methoxycarbonyloxy, acetyloxy, hydroxyl, methoxy, ethoxy or dimethylamino, cyclohexyl, benzyl, phenyl, which can be substituted by chlorine, cyano, methyl, ethyl, methoxy or ethoxy, or 2,2,6,6-tetramethyl-or 1,2,2,6,6-pentamethyl-piperidin-4-yl, Y$^{12'}$ denotes hydrogen or has the meaning of Y$^{12}$, or NY$^{12}$Y$^{12'}$ represents a pyrrolidino, piperidino, piperazino, morpholino or pyrazolino radical which is substituted by C$_1$–C$_4$-alkyl and/or phenyl, which can also carry chlorine, methyl, methoxy, ethoxy or cyano.

6. A chromogenic 3,1-benzoazine according to claim 2, wherein the substitutent for NY$^4$Y$^5$ is phenyl.

* * * * *

UNITED STATES PATENT AND TRADEMARK OFFICE
CERTIFICATE OF CORRECTION

PATENT NO. : 4,835,270
DATED : May 30, 1989
INVENTOR(S) : Horst Berneth

It is certified that error appears in the above-identified patent and that said Letters Patent is hereby corrected as shown below:

| | |
|---|---|
| Title Page, No. 22:Filed | Delete "1988" and substitute --1985-- |
| Col. 2, line 39 | Delete "aryol" and substitute --aroyl-- |
| Col. 3, line 20 | Correct spelling of --phosphate-- |
| Col. 4, line 62 | Delete "process" and substitute --processes-- |
| Col. 4, line 65 | Delete "2,700.937" and substitute --2,700,937-- |
| Col. 7, line 5 | Delete "alkoxyl" and substitute --alkoxy-- |
| Col. 7, line 38 | Delete "alkeyl" and substitute --alkyl-- |
| Col. 10, line 31 | After "3,1" insert -- - -- |
| Col. 13, line 35 | Correct --fabrics-- |
| Col. 14, line 39 | Correct spelling of --turquoise-- |
| Col. 19, line 28 | Before "450" insert -- = -- |
| Col. 29, line 34 | Delete "$\propto 2$" and substitute --$\Delta^2$-- and "in" should be --is-- |
| Col. 31, lines 24-25 | Correct spelling of --phosphorus-- |
| Col. 32, line 30 | After "39" delete "to" and substitute --or-- |
| Col. 33, line 61 | Delete "dired" and substitute --dried-- |
| Col. 46, line 67 | Delete " be" and substitute --by-- |
| Col. 50, lines 16, 18 | Correct spelling of --alkyl-- |

UNITED STATES PATENT AND TRADEMARK OFFICE
CERTIFICATE OF CORRECTION

PATENT NO. : 4,835,270

DATED : May 30, 1989

INVENTOR(S) : Horst Berneth

It is certified that error appears in the above-identified patent and that said Letters Patent is hereby corrected as shown below:

Col. 50, line 17           Correct spelling of --piperidyl--

Col. 52, line 26           Correct spelling of --ethyl--

Signed and Sealed this

Seventh Day of August, 1990

Attest:

HARRY F. MANBECK, JR.

*Attesting Officer*      Commissioner of Patents and Trademarks